(12) United States Patent
Eibl et al.

(10) Patent No.: US 6,649,780 B1
(45) Date of Patent: Nov. 18, 2003

(54) CATIONIC LIPIDS

(75) Inventors: Hansjörg Eibl, Bovenden (DE); Jinkang Wang, San Francisco, CA (US); Yi Lin Zhang, Woodside, CA (US)

(73) Assignees: Valentis, Inc., Burlingame, CA (US); Max-Planck-Gesellschaft zur Foerderung der Wissaschaften B.V., Berlin (DE)

( * ) Notice: Subject to any disclaimer, the term of this patent is extended or adjusted under 35 U.S.C. 154(b) by 0 days.

(21) Appl. No.: 09/465,562

(22) Filed: Dec. 17, 1999

Related U.S. Application Data

(60) Provisional application No. 60/113,416, filed on Dec. 22, 1998.

(51) Int. Cl.[7] ............................................. C04C 14/03
(52) U.S. Cl. ..................... 554/110; 554/103; 554/108; 554/109; 564/483; 564/503; 564/506; 564/508; 568/589
(58) Field of Search .................................. 554/103, 104, 554/105, 108, 110; 568/599, 589; 564/463, 503, 506, 508

(56) References Cited

PUBLICATIONS

Chem. Abstr. of JP–54/117421, publication date 1979.*
Chem. Abstr. of WO–94/21595, publication date 1994.*

\* cited by examiner

*Primary Examiner*—Deborah D. Carr
(74) *Attorney, Agent, or Firm*—Townsend and Townsend and Crew LLP

(57) ABSTRACT

Cationic lipids are provided which are useful in the preparation of liposomes and other lipid vesicle carriers. The lipids of the invention are particularly useful as carriers of nucleic acids and other negatively charged substances, for delivery to cells.

18 Claims, 10 Drawing Sheets

IIIA.1: RCOO = 14:0
IIIA.2: RCOO = 18:1

IIIA

IIIB.1: RCOO = 14:0
IIIB.2: RCOO = 18:1

IIIB

IVA

Size of DNA-liposome Complexes

CATIONIC LIPIDS

CROSS-REFERENCE TO RELATED APPLICATIONS

This application claims priority to U.S. Provisional Patent Application No. 60/113,416, filed Dec. 22, 1998, the disclosure of which is hereby incorporated by reference in its entirety for all purposes.

FIELD OF THE INVENTION

This invention relates to novel lipids which in some embodiments are neutral and glycerol based, and in some embodiments are cationic. The lipids are useful in the preparation of liposomes and other lipid vesicle carriers of nucleic acids and other substances, for delivery to cells.

BACKGROUND OF THE INVENTION

The introduction of genetic material into a cell can facilitate expression of an encoded protein to complement a deficient or defective protein. The use of such technology allows for the treatment of disease as well as production of certain proteins in an in vitro application.

One method of introducing nucleic acids into a cell is mechanically, using direct microinjection. However this method is only practical for transfecting eukaryotic germline cells for the production of transgenic systems. To be effective in treating a disease, a nucleic acid-based therapy typically must enter many cells.

Gene transfer entails distributing nucleic acids to target cells and then transferring the nucleic acid across a target cell membrane intact and in a form that can function in a therapeutic manner. In vivo gene transfer is complicated by serum interactions, immune clearance, toxicity and biodistribution.

The in vivo gene transfer methods under study in the clinic consist almost entirely of viral vectors. Although viral vectors have the inherent ability to transport nucleic acids across cell membranes and some can integrate exogenous DNA into the chromosomes, they can carry only limited amounts of DNA and also pose risks. One such risk involves the random integration of viral genetic sequences into patient chromosomes, potentially damaging the genome and possibly inducing a malignant transformation. Another risk is that the viral vector may revert to a pathogenic genotype either through mutation or genetic exchange with a wild-type virus.

More recently, cationic lipids have been used to deliver nucleic acids to cells, allowing uptake and expression of foreign genes both in vivo and in vitro. While the mechanism by which cationic lipid carriers act to mediate transfection is not clearly understood, they are postulated to act in a number of ways with respect to both cellular uptake and intracellular trafficking. Some of the proposed mechanisms by which cationic lipids enhance transfection include: (i) compacting the DNA, protecting it from nuclease degradation and enhancing receptor-mediated uptake, (ii) improving association with negatively-charged cellular membranes by giving the complexes a positive charge, (iii) promoting fusion with endosomal membranes facilitating the release of complexes from endosomal compartments, and (iv) enhancing transport from the cytoplasm to the nucleus where DNA may be transcribed. When used for in vivo delivery, the role of the cationic lipid carriers is further complicated by the interactions between the lipid-nucleic acid complexes and host factors, e.g., the effects of the lipids on binding of blood proteins, clearance and/or destabilization of the complexes.

Typically, cationic lipids are mixed with a non-cationic lipid, usually a neutral lipid, and allowed to form stable liposomes, which liposomes are then mixed with the nucleic acid to be delivered. The liposomes may be large unilamellar vesicles (LUVs), multilamellar vesicles (MLVs) or small unilamellar vesicles (SUVs). The liposomes are mixed with nucleic acid in solution, at concentrations and ratios optimized for the target cells to be transfected, to form cationic lipid-nucleic acid transfection complexes. Alterations in the lipid formulation allow preferential delivery of nucleic acids to particular tissues in vivo. PCT patent application numbers WO 96/40962, WO 96/40963. Certain preformed cationic liposome compositions are available, such as LIPOFECTIN® and LIPOFECTAMINE®. Another method of complex formation involves the formation of DNA complexes with mono- or poly-cationic lipids without the presence of a neutral lipid. These complexes are often not stable in water. Additionally, these complexes are adversely affected by serum (see, Behr, *Acc. Chem. Res.* 26:274–78 (1993)). An example of a commercially available poly-cationic lipid is TRANSFECTAM®.

While the use of cationic lipid carriers for transfection is now well established, structure activity relationships are not well understood. It is postulated that different lipid carriers will affect each of the various steps in the transfection process (e.g., condensation, uptake, nuclease protection, endosomal release, nuclear trafficking, and decondensation) with greater or lesser efficiency, thereby making the overall transfection rate difficult to correlate with lipid structures. Thus, alterations in either the cationic or neutral lipid component do not have easily predictable effects on activity. For the most part, therefore, improvements to known cationic lipid-mediated delivery systems are dependent on empirical testing. When intended for in vivo transfection, new lipids and lipid formulations should be screened in vivo to accurately predict optimal lipids and formulations for transfection of target cells.

More recently, new cationic lipids have been prepared which exhibit excellent transfection properties when formulated with nucleic acids. See, for instance, WO 95/14380 the disclosure of which is incorporated herein by reference. The compositions provided in WO 95/14380 are metabolizable in animal cells to components that are typically endogenous to the cells. Despite the properties associated with the novel cationic lipids, there exists a need for cationic lipids which are more hydrolytically stable in serum and which can be formulated into suitable transfection compositions. The present invention provides such cationic lipids, along with methods for their preparation and use in lipid-based compositions.

Relevant Literature

Cationic lipid carriers have been shown to mediate intracellular delivery of plasmid DNA (Felgner, et al., (1987) *Proc. Natl. Acad Sci.* (USA), 84:7413–7416); mRNA (Malone, et al., (1989) *Proc. Natl. Acad. Sci.* (USA) 86:6077–6081); and purified transcription factors (Debs, et al., (1990) *J. Biol. Chem.* 265:10189–10192), in functional form. Literature describing the use of lipids as carriers for DNA include the following: Zhu, et al., (1993) *Science*, 261:209–211; Vigneron, et al., (1996) *Proc. Natl. Acad. Sci.* USA, 93:9682–9686; Hofland, et al., (1996) *Proc. Natl. Acad. Sci.* USA, 93:7305–7309; Alton, et al., (1993) *Nat. Genet.* 5:135–142; von der Leyen, et al., (1995) *Proc. Natl. Acad. Sci.* (USA), 92:1137–1141 ; See also Stribling, et al., (1992) *Proc. Natl. Acad. Sci.* (USA) 89:11277–11281, which reports the use of lipids as carriers for aerosol gene delivery to the lungs of mice. For a review of liposomes in gene therapy, see Lasic and Templeton, (1996) *Adv. Drug Deliv. Rev.* 20:221–266.

The role of helper or neutral lipids in cationic lipid-mediated gene delivery is described in Felgner, et al., (1994) *J. Biol. Chem.* 269(4):2550–2561 (describing improved transfection using DOPE); and Hui, et al., (1996) *Biophys. J.* 71:590–599. The effect of cholesterol on liposomes in vivo is described in Semple, et al., (1996) Biochem. 35(8): 2521–2525.

SUMMARY OF THE INVENTION

In one aspect, the present invention provides compounds having the formula:

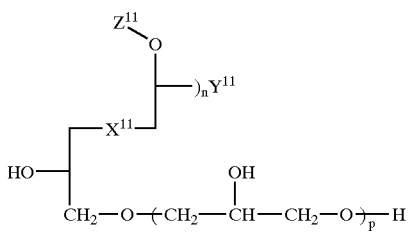

(I)

In this formula, $X^{11}$ represents a radical selected from the group consisting of

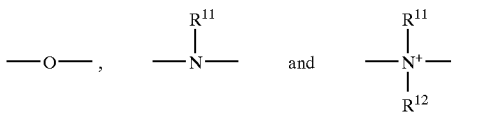

(Ia)

in which $R^{11}$ and $R^{12}$ are each independently H or a $C_1$–$C_6$ alkyl group. The symbol $Z^{11}$ represents H, a saturated $C_1$–$C_{26}$ alkyl group, an unsaturated $C_3$–$C_{26}$ alkyl group, a saturated $C_2$–$C_{26}$ acyl group, or an unsaturated $C_4$–$C_{26}$ acyl group. The subscript n represents the integer 1 or 2. The subscript p represents a value between 0 to 6. When n is 1, $Y^{11}$ is a monovalent radical selected from

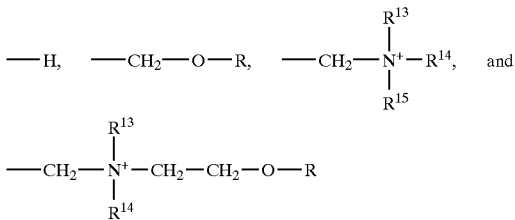

in which R is H, a saturated $C_1$–$C_{26}$ alkyl group, an unsaturated $C_3$–$C_{26}$ alkyl group, a saturated $C_2$–$C_{26}$ acyl group, or an unsaturated $C_4$–$C_{26}$ acyl group, providing at least one of either R or $Z^{11}$ contains a group having at least 14 carbon atoms. $R^{13}$, $R^{14}$ and $R^{15}$ are each independently a $C_1$–$C_6$ alkyl group. When n is 2, $Y^{11}$ is a divalent radical of formula:

(Ia)

in which $X^{12}$ and $X^{13}$ are radicals independently selected from

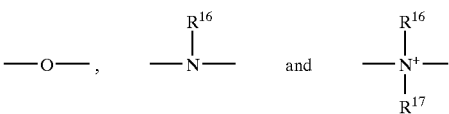

in which $R^{16}$ and $R^{17}$ are each independently H or a $C_1$–$C_6$ alkyl group; and m is an integer of from 2 to 12.

In another aspect, the present invention provides compounds having the formula:

$$W^{21}-Y^{21}-W^{21}- \qquad (II)$$

in which $Y^{21}$ is —O— or —O—$CH_2$—CH(OH)—$CH_2$—O—; and each $W^{21}$ is independently a radical of formula:

(IIa)

in which $X^{21}$ is selected from

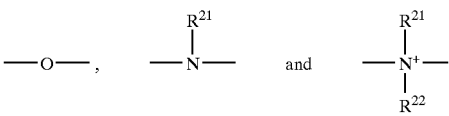

which $R^{21}$ and $R^{22}$ are each independently H or a $C_1$–$C_6$ alkyl group. In formula (IIa), the symbol $Z^{21}$ represents a $C_{14}$–$C_{26}$ saturated or unsaturated alkyl or a $C_{14}$–$C_{26}$ saturated or unsaturated acyl group.

In yet another aspect, the present invention provides compounds having the formula:

$$L^{31}-Y^{31}-L^{31} \qquad (III)$$

In formula (III), each $L^{31}$ represents a radical, which may be the same, or different having the formula

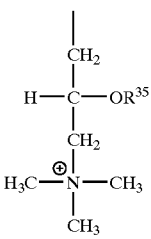

wherein $R^{35}$ represents a $C_8$–$C_{26}$ saturated or unsaturated alkyl group, or a $C_8$–$C_{26}$ saturated or unsaturated acyl group, provided at least one $L^{31}$ comprises an alkyl or acyl chain of at least 14 carbons in length. $Y^{31}$ represents a radical selected from

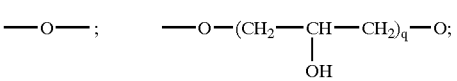

the subscript q represents an integer from 1 to 5.

In still another aspect, the present invention provides compounds having the formula:

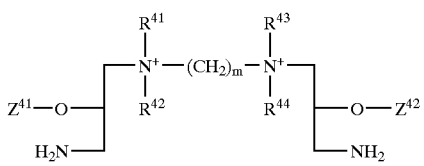

(IV)

in which $Z^{41}$ and $Z^{42}$ each independently represents H, a saturated $C_1$–$C_{26}$ alkyl group, an unsaturated $C_3$–$C_{26}$ alkyl group, a saturated $C_2$–$C_{26}$ acyl group, or an unsaturated $C_4$–$C_{26}$ acyl group providing at least one of either $R^{41}$ or $R^{42}$ contains a group having at least 14 carbon atoms. $R^{41}$, $R^{42}$, $R^{43}$ and $R^{44}$ are each independently H or a $C_1$–$C_6$ alkyl group; and m is an integer of from 2 to 12.

In addition to each of the above compounds, the present invention provides compositions containing one or more of those compounds. The compositions are typically in the form of liposomes or other lipid vesicle carriers. Still further, the present invention provides compositions containing one or more of the above compounds, typically in a lipid vesicle formulation, in admixture with a therapeutic agent (e.g., antibacterial agents, anticancer agents, nucleic acids, and the like).

DETAILED DESCRIPTION OF THE INVENTION AND SPECIFIC EMBODIMENTS

Abbreviations

Figure 1:
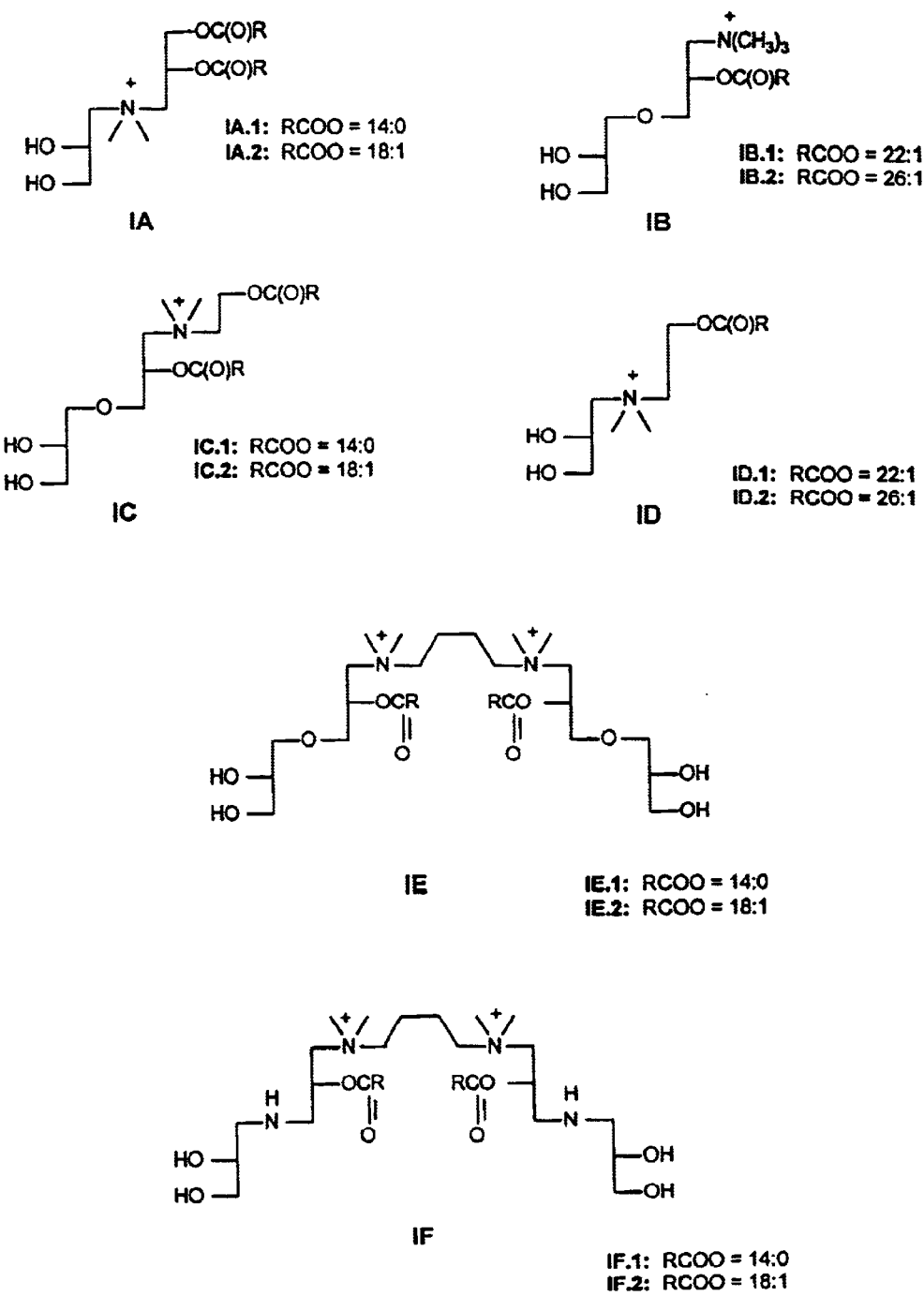
FIG. 1 displays preferred embodiments for compounds of Formula I.

The abbreviations used herein have the following meanings: DOTIM, 1-[2-(9(z))-octadecenoyloxy)ethyl]-2-(8(z))-heptadecenoyl-3-(2-hydroxyethyl)imidazolinium chloride; EDTA, ethylenediaminetetraacetic acid; CAT, chloramphenicol aminotransferase; D5W, 5% (w/v) dextrose in water; HCMV, human cytomegalovirus; CHOL, cholesterol; DLPE, dilauroylphosphatidylethanolamine; IV, intravenous; CBC, complete blood count;

All numerical ranges in this specification and claims are intended to be inclusive of their upper and lower limits.

Embodiments of the Invention

Compounds of Formula (I)

As noted in the Summary, the present invention provides novel compounds which are useful as lipids in the formation of lipid vesicle carriers, typically in admixture with other lipids containing at least 2 free hydroxyl groups per molecule.

In a first aspect, the present invention provides compounds which are represented by Formula (I):

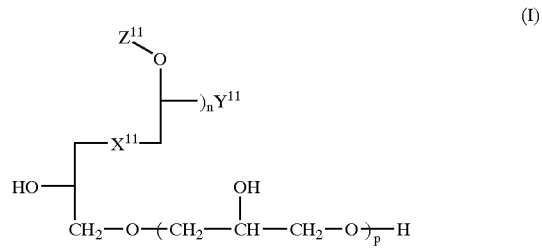

(I)

In this formula, $X^{11}$ represents a radical selected from the group consisting

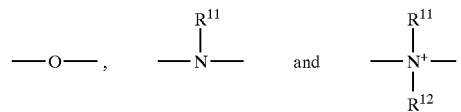

in which $R^{11}$ and $R^{12}$ are each independently H or a $C_1$–$C_6$ alkyl group; $Z^{11}$ represents H, a saturated $C_1$–$C_{26}$ alkyl group, an unsaturated $C_3$–$C_{26}$ alkyl group, a saturated $C_2$–$C_{26}$ acyl group, or an unsaturated $C_4$–$C_{26}$ acyl group. The subscript n represents the integer 1 or 2. The subscript p represents a value between 0 to 6. When n is 1, $Y^{11}$ is a monovalent radical selected from

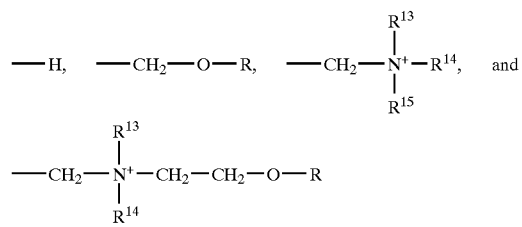

in which R is H, a saturated $C_1$–$C_{26}$ alkyl group, an unsaturated $C_3$–$C_{26}$ alkyl group, a saturated $C_2$–$C_{26}$ acyl group, or an unsaturated $C_4$–$C_{26}$ acyl group providing at least one of either R or $Z^{11}$ contains a group having at least 14 carbon atoms. $R^{13}$, $R^{14}$ and $R^{15}$ are each independently a $C_1$–$C_6$ alkyl group. (see, FIG. 1, structures IA–ID). When n is 2, $Y^{11}$ is a divalent radical of formula:

$$-CH_2-X^{12}-(CH_2)_m-X^{13}-CH_2- \quad (Ia)$$

in which $X^{12}$ and $X^{13}$ are radicals independently selected from

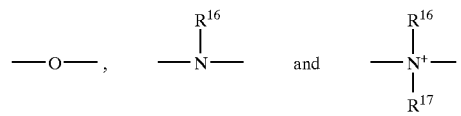

in which $R^{16}$ and $R^{17}$ are each independently H or a $C_1$–$C_6$ alkyl group; and m is an integer of from 2 to 12. (see, FIG. 1, structures IE–IF).

For the compounds described herein, the term "alkyl" refers to a hydrocarbon radical which may be straight-chain or branched-chain (for example, methyl, ethyl, propyl, isopropyl). Preferred alkyl groups for some substituents are lower alkyl groups containing 1 to 6 carbon atoms. Within the group of $C_1$–$C_6$ alkyl groups, methyl, ethyl and propyl are particularly preferred with methyl being the most preferred. For other alkyl group substituents, long chain alkyl groups containing from 8 to 26 carbon atoms are preferred. Additionally, for the long chain ($C_8$–$C_{26}$) alkyl groups, the hydrocarbon chain can be either saturated or unsaturated. Examples of suitable saturated hydrocarbon chains include those chains derived from fatty acids or alcohols, for example, lauryl (C12:0), myristyl (C14:0), palmityl (C16:0), stearyl (C18:0), arachidyl (C20:0), and behenyl (C22:0). Examples of suitable unsaturated hydrocarbon chains include, for example, oleyl (C18:1,cis-9), linoleyl (C18:2,cis-9,12), elaidyl (C18:1,trans-9), linolelaidyl (C18:2,trans-9,12), eicosenyl (C20:1,cis-11), and the like. In each of the above, the configuration is provided as, for example, (C20:1, cis-11), indicating a twenty carbon chain having a single cis double bond between the eleventh and twelfth carbon atoms (when counting the carbon atoms in the conventional manner for fatty acids). While examples are provided for saturated and unsaturated hydrocarbon chains having an even number of carbon atoms, the invention is not so limited. A variety of methods are available to the skilled chemist for a one-carbon homologation or degradation to provide hydrocarbon chains having an odd number of carbon atoms, or to choose a complete synthetic strategy.

Similarly, the term "acyl" refers to a radical produced from an organic acid by removal of the hydroxyl group. Examples of $C_2$–$C_{26}$ acyl radicals include acetyl, lauroyl, palmitoyl, stearoyl, myristoyl, oleoyl and erucoyl.

In one group of preferred embodiments, $X^{11}$ is —O—. In another group of preferred embodiments, $X^{11}$ is —N$^+$(CH$_3$)$_2$—. For those embodiments in which $X^{11}$ is —O— and n is 1, $Y^{11}$ is preferably —CH$_2$—N$^+$(CH$_3$)$_3$. For those embodiments in which $X^{11}$ is —O— and n is 2, $Y^{11}$ is preferably —CH$_2$—N(CH$_3$)$_2$—CH$_2$CH$_2$CH$_2$CH$_2$—N$_+$(CH$_3$)$_2$—. For those embodiments in which $X^{11}$ is —N$^+$(CH$_3$)$_2$— and n is 1, $Y^{11}$ will preferably be —H, —CH$_2$—O—R, or —CH$_2$—O—C(=O)R. For those embodiments in which $X^{11}$ is —NH— and n is 2, $Y^{11}$ is preferably —CH$_2$—N$^+$(CH$_3$)$_2$—CH2CH2CH2CH2—N$^+$(CH$_3$)$_2$—CH$_2$—.

Compounds described herein having at least one formal positive charge will typically be associated with an anion, A-, preferably a pharmaceutically acceptable anion. As used herein, the term "pharmaceutically acceptable anion" refers to anions of organic and inorganic acids which provide non-toxic salts in pharmaceutical preparations. Examples of such anions include chloride, bromide, sulfate, phosphate, acetate, benzoate, citrate, glutamate, and lactate. The preparation of pharmaceutically acceptable salts is described in Berge, et al., *J. Pharm. Sci.* 66:1–19 (1977), incorporated herein by reference. Preferably, A- is chloride, bromide or citrate.

Structures of the preferred compounds of Formula (I) are provided in FIG. 1, for compounds IA, IB, IC, ID, IE and IF.

Compounds of Formula (II)

In a second aspect, the present invention provides compounds of Formula (II).

$$W^{21}\text{—}Y^{21}\text{—}W^{21} \qquad (II)$$

In formula (II), the symbol $Y^{21}$ represents —O— or —O—CH$_2$—CH(OH)—CH$_2$—O—. Each of the symbols $W^{21}$ independently represent a radical of formula:

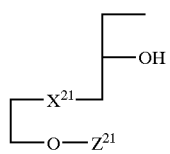

(IIa)

in which $X^{21}$ is selected from

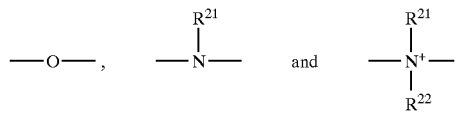

The symbols $R^{21}$ and $R^{22}$ each independently represent H or a $C_1$–$C_6$ alkyl group. Particularly preferred alkyl groups are methyl, ethyl and propyl, with methyl being the most preferred. In formula (IIa), the symbol $Z^{21}$ represents a $C_8$–$C_{26}$ saturated or unsaturated alkyl or a $C_8$–$C_{26}$ saturated or unsaturated acyl group. Preferred $C_8$–$C_{26}$ acyl groups are myristoyl and oleoyl. Preferred $C_8$–$C_{26}$ alkyl groups are myristyl and oleyl.

In one group of preferred embodiments, $X^{21}$ is a radical of formula

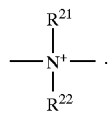

More preferably $X^{21}$ is —N$^+$(CH$_3$)$_2$. Within this group of embodiments, particularly preferred are those in which $Y^{21}$ is —O—, $X^{21}$ is —N$^+$(CH$_3$)$_2$—, and $Z^{21}$ is $C_{12}$–$C_{20}$ saturated or unsaturated acyl. Also preferred are those in which $Y^{21}$ is —O—, $X^{21}$ is —N$^+$(CH$_3$)$_2$—, and $Z^{21}$ is $C_{12}$–$C_{20}$ saturated or unsaturated alkyl. Still other preferred embodiments are those in which $Y^{21}$ is —O—CH$_2$—CH(OH)—CH$_2$—O—, $X^{21}$ is —N$^+$(CH$_3$)$_2$—, and $Z^{21}$ is $C_{12}$–$C_{20}$ saturated or unsaturated acyl, and those in which $Y^{21}$ is —O—CH$_2$—CH(OH)—CH$_2$—O—, $X^{21}$ is —N$^+$(CH$_3$)$_2$—, and $Z^{21}$ is $C_{12}$–$C_{20}$ saturated or unsaturated alkyl.

Figure 2:
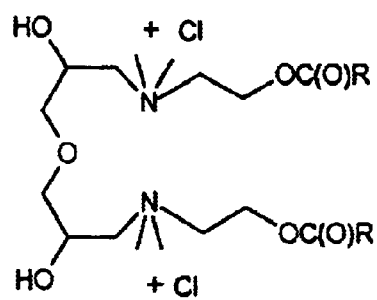
FIG. 2 provides preferred embodiments for compounds of Formula II.
Figure 2:
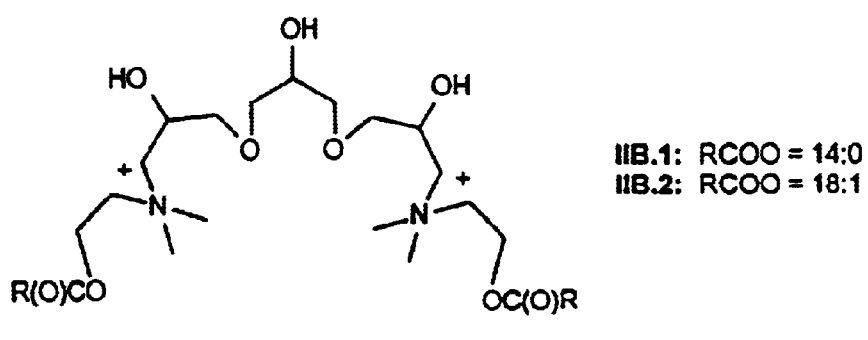
Figure 3:
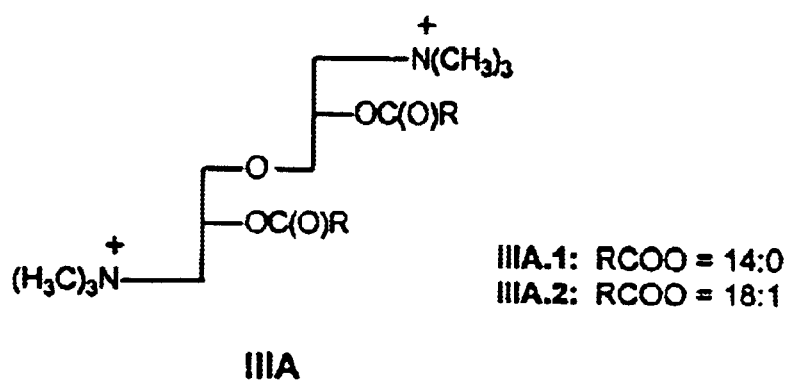
FIG. 3 provides preferred embodiments for compounds of Formula III.
Figure 3:
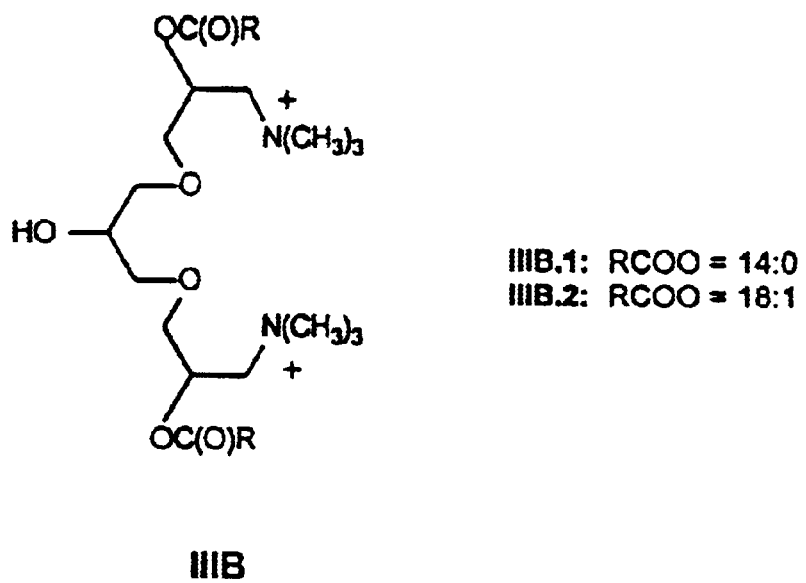

Structures for some of the preferred compounds of formula (II) are provided in FIG. 2, as compounds IIA and IIB.

Compounds of Formula (III)

In a third aspect, the present invention provides compounds of formula (III):

$$L^{31}\text{—}Y^{31}\text{—}L^{31} \qquad (III)$$

In formula (III), each $L^{31}$ represents a radical, which may be the same or different having the formula

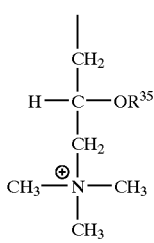

wherein $R^{35}$ represents a $C_8$–$C_{26}$ saturated or unsaturated alkyl group or a $C_8$–$C_{26}$ saturated or unsaturated acyl group provided at least one $L^{31}$ comprises an alkyl or acyl chain of at least 14 carbons in length. $X^{31}$ represents a radical selected from

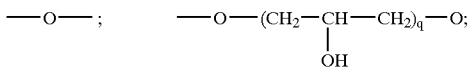

the subscript q representation an integer from 1 to 5.

Compounds of Formula (IV)

In a fourth aspect, the present invention provides compounds having the formula:

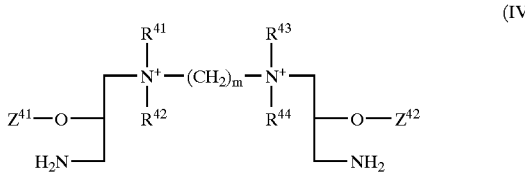

In this formula, each of $Z^{41}$ and $Z^{42}$ independently represents H, a saturated $C_1$–$C_{26}$ alkyl group, an unsaturated $C_3$–$C_{26}$ alkyl group, a saturated $C_2$–$C_{26}$ acyl group, or an unsaturated $C_4$–$C_{26}$ acyl group providing at least one of either $R^{41}$ or $R^{42}$ contains a group having at least 14 carbon atoms. $R^{41}$, $R^{42}$, $R^{43}$ and $R^{44}$ each independently represent H or a $C_1$–$C_6$ alkyl group; and m is an integer of from 2 to 12.

In preferred embodiments, $R^{41}$, $R^{42}$, $R^{43}$ and $R^{44}$ each independently represent a $C_1$–$C_3$ alkyl group, most preferably a methyl group. Preferred integers for m are from 3 to 5, with 4 being the most preferred. Among the groups provided for $Z^{41}$ and $Z^{42}$, preferred are the $C_{12}$–$C_{20}$ saturated or unsaturated alkyl groups and the $C_2$–$C_{20}$ saturated or unsaturated acyl groups. Most preferred are those groups (alkyl or acyl) having from about 14 to about 18 carbon atoms in a straight chain.

Figure 4:
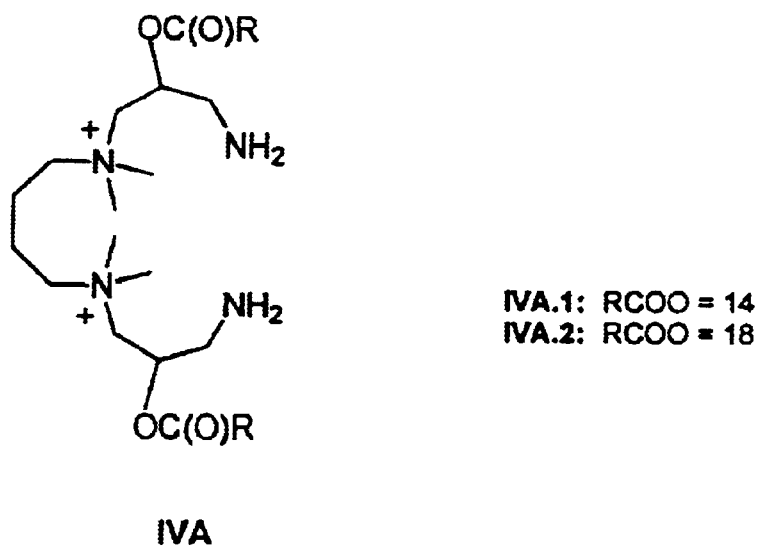
FIG. 4 provides preferred embodiments for compounds of Formula IV.

Structures of species of Formula (IV) are provided in FIG. 4, as compounds IVA and IVB.

Preparation of the Compounds of Formulae (I) to (IV)

Figure 5:
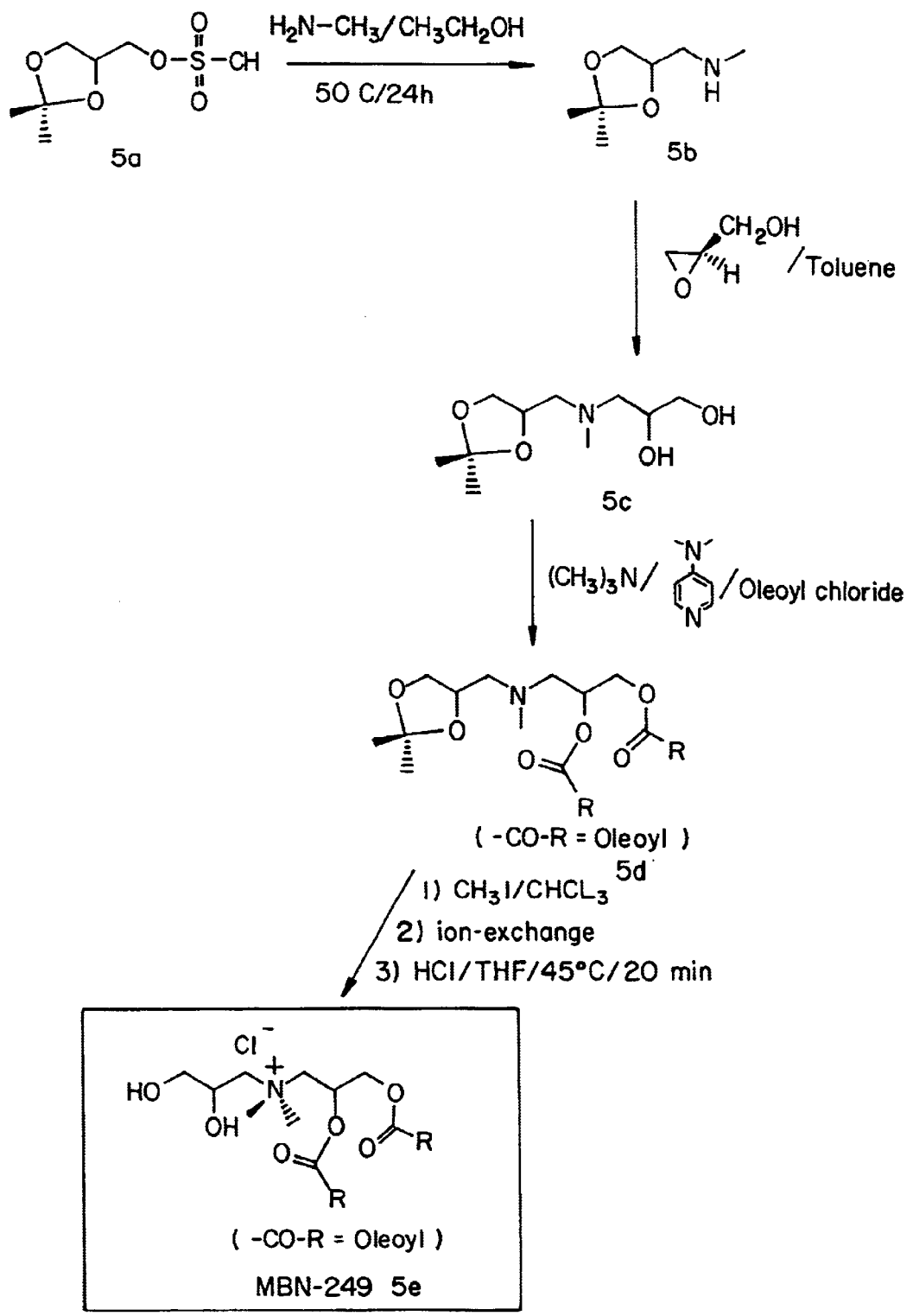
FIG. 5 provides a procedure for the synthesis of compounds of Formula I wherein R is acyl.

Preparation of lipids of Formula (I) can be carried out using procedures similar to those outlined in FIG. 5 for compounds in which $X^{11}$ is —$N^+(CH_3)_2$—, n is 1, $Y^{11}$ is —$CH_2$—O—C(=O)R and $Z^{11}$ is a $C_8$–$C_{26}$ saturated or unsaturated acyl group. Briefly, the hydroxy group of 2,2-dimethyl-1,3-dioxane-4-methanol is converted to a leaving group using a reagent such as methanesulfonyl chloride to provide 5a. Displacement of the sulfonate ester group is accomplished with methylamine (or other suitable amines) to provide 5b. Treatment of 5b with glycidol provides compound 5c. Acylation of the hydroxy groups is accomplished using standard methods with essentially any commercially available acid or acid chloride to provide 5d. Alkylation of the amine group and removal of the acetonide protecting group provides a target compound 5e.

Figure 6:
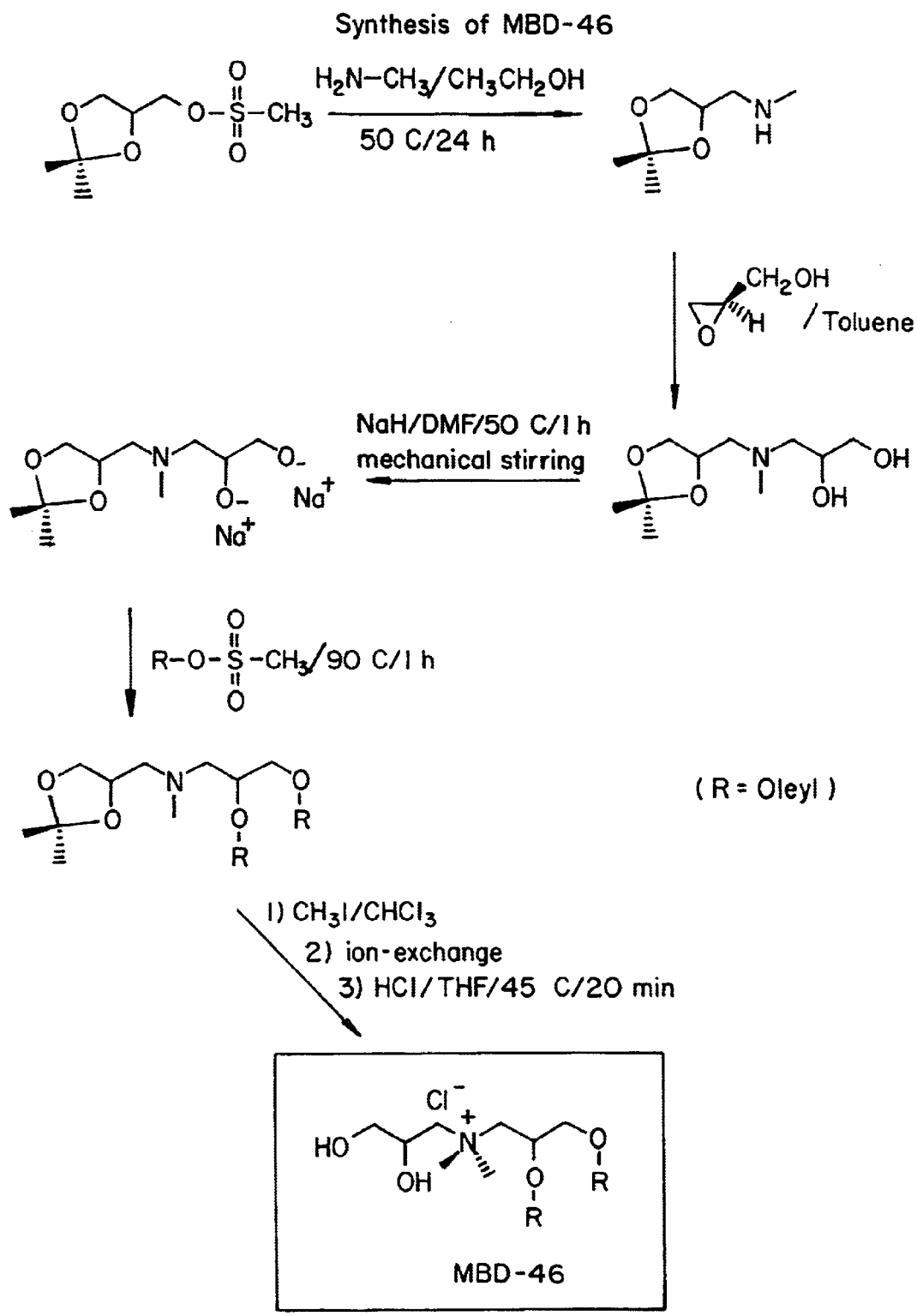
FIG. 6 provides a procedure for the synthesis of compounds of Formula I wherein R is alkyl.

Formation of compounds related to 5e in which the acyl groups are replaced with $C_8$–$C_{24}$ alkyl groups can be accomplished beginning with 5c (see FIG. 6). The salt formed using the procedures in FIG. 1 is a chloride salt. Replacement of the chloride ion with another anion can be accomplished using, for example ion exchange resins which are equilibrated with the desired anion. However, even more preferred is to start with 1,2-dialkylglycerols using the above sequence of reactions 5a through 5c. The yields are better and configurationally pure compounds can be obtained from the respective starting 1,2-dialkylglycerols.

As will be apparent to those of skill in the art, certain of the compounds described herein have chiral centers and therefore can exist as an optically pure enantiomer, a racemic mixture or various percentages of one or more enantiomers. All such compounds are within the scope of the present invention.

Lipid Vesicle Compositions

In another aspect, the present invention provides lipid vesicle compositions which contain a compound of Formulae (I)–(IV), above. The lipid vesicle compositions will typically be in the form of liposomes (e.g., unilammelar vesicles, multilammelar vesicles), or other lipid bilayer forms. The compounds described above can be used alone or combined with other lipids in the preparation of compositions useful in intracellular delivery systems (e.g., transfection systems), or other conventional drug delivery systems.

A variety of other lipids are suitable for use in the present compositions. As used herein, the term "lipid" refers to any suitable material resulting in a bilayer in aqueous solution such that a hydrophobic portion of the lipid material orients toward the bilayer while a hydrophilic portion orients toward the aqueous phase. Hydrophilic characteristics derive from the presence of phosphato, carboxylic, sulfato, amino, sulfhydryl, nitro, and other like groups. Hydrophobicity is conferred by the inclusion of groups that include, but are not limited to, long chain saturated and unsaturated aliphatic hydrocarbon groups, with such groups being optionally substituted by one or more aromatic, cycloaliphatic or heterocyclic group(s). The preferred lipids for use in conjunction with the cationic lipids of formulae (I)–(IV) are phosphoglycerides, sphingolipids and sterols (e.g. cholesterol), representative examples of which include diacyl derivatives of phosphatidylcholine, phosphatidylethanolamine, phosphatidylserine, phosphatidylinositol and phosphatidic acid (e.g., palmitoyloleoyl phosphatidylcholine, dipalmitoylphosphatidylcholine, dioleoylphosphatidylcholine, distearoylphosphatidylcholine and dilinoleoylphosphatidylcholine) and the related lysophosphatidylcholine and lysophosphatidylethanolamine. Still other lipids are useful, such as sphingolipid and glycosphingolipid families. Additionally, the lipids described above may be mixed with other lipids (co-lipids) including triglycerides and sterols (e.g., cholesterol).

When the lipid vesicle compositions are in the form of liposomes, the compounds of formulae (I)–(IV) will typically be combined with other lipids, including neutral lipids, zwitterionic lipids, anionic lipids or other cationic lipids known to those of skill in the art. Preferably, the compositions will comprise other neutral lipids or anionic lipids (e.g., cholesterol, dilaurylphosphatidylethanolamine). Particularly preferred co-lipids include DOPE, DLPE and cholesterol. For systemic delivery of nucleic acids, cholesterol is the preferred co-lipid.

In general, less saturated lipids are more easily sized, particularly when the liposomes must be sized below about 0.3 microns, for purposes of filter sterilization. In one group of embodiments, lipids containing saturated fatty acids with carbon chain lengths in the range of $C_{14}$ to $C_{22}$ are preferred. In another group of embodiments, lipids with mono- or di-unsaturated fatty acids with carbon chain lengths in the range of $C_{14}$ to $C_{22}$ are used. Additionally, lipids having mixtures of saturated and unsaturated fatty acid chains can be used.

A number of methods are available for preparing liposome compositions (see, for example, Szoka, et al., *Ann. Rev. Biophys. Bioeng.* 9:467 (1980), U.S. Pat. Nos. 4,235,871, 4,501,728, 4,837,028, the text Liposomes, Marc J. Ostro, ed., Marcel Dekker, Inc., New York, 1983, Chapter 1, and Hope, et al., *Chem. Phys. Lip.* 40:89 (1986), all of which are incorporated herein by reference). One method produces multilamellar vesicles of heterogeneous sizes. In this method, the vesicle-forming lipids are dissolved in a suitable organic solvent or solvent system and dried under vacuum or an inert gas to form a thin lipid film. If desired, the film may be redissolved in a suitable solvent, such as tertiary butanol, and then lyophilized to form a more homogeneous lipid mixture which is in a more easily hydrated powder-like form. This film is covered with an aqueous buffered solution and allowed to hydrate, typically over a 15–60 minute period with agitation. The size distribution of the resulting multilamellar vesicles can be shifted toward smaller sizes by hydrating the lipids under more vigorous agitation conditions.

Following liposome preparation, the liposomes may be sized to achieve a desired size range and relatively narrow distribution of liposome sizes. A size range of about 0.2–0.4 microns allows the liposome suspension to be sterilized by filtration through a conventional filter, typically a 0.22 micron filter. The filter sterilization method can be carried out on a high through-put basis if the liposomes have been sized down to about 0.2–0.4 microns.

Techniques for sizing liposomes to a desired size, include sonication (see, U.S. Pat. No. 4,737,323, incorporated herein by reference), extrusion through small-pore polycarbonate membranes or an asymmetric ceramic membrane, and homogenization. Homogenization relies on shearing energy to fragment large liposomes into smaller ones. In a typical homogenization procedure, multilamellar vesicles are recirculated through a standard emulsion homogenizer until selected liposome sizes, typically between about 0.1 and 0.5 microns, are observed. In any of the methods, the liposome size distribution can be monitored by conventional laser-beam particle size discrimination.

The lipid vesicle compositions will, in some embodiments, have an attached targeting moiety. For example, a ligand binding specifically to a receptor on a particular target cell type can be used to target delivery of the lipid carrier (with, e.g., the DNA or antibiotic of interest) to the desired target cells. Alternatively, the active compound may be a peptide or other small molecule designed to regulate intracellular trafficking of the delivered substance, e.g., triggering endosomal release or transport into the nucleus using a nuclear localizing sequence.

The active compounds bound to the lipid mixture can vary widely, from small haptens (molecular weights of about 125 to 2000) to antigens (molecular weights ranging from around 6000 to 1 million). Of particular interest are proteinaceous ligands that bind to and are internalized by specific complementary binding partners on cell surfaces. Illustrative active compounds include cytokines, interferons, hormones, asialoglycoprotein antibodies to cell surface receptors or other molecules, and fragments of such compounds that retain the ability to bind to the same cell surface binding partners that bind the original (non-fragment) molecules.

The number of active compounds bound to a lipid carrier will vary with the size of the complex, the size of the compound, the binding affinity of the molecule to the target cell receptor or ligand, and the like. Usually, the bound active molecules will be present in the lipid mixture in from about 0.001 to 10 mole percent, more usually from about 0.01 to 5 mole percent based on the percent of bound molecules to the total number of molecules available in the mixture for binding.

Lipid-Nucleic Acid Compositions

In another aspect, the present invention provides lipid-nucleic acid compositions in which the lipid portion comprises at least one cationic lipid of the invention.

The nucleic acids which are useful in the present invention are typically nucleotide polymers having from 10 to 100,000 nucleotide residues. Typically, the nucleic acids are to be administered to a subject for the purpose of repairing or enhancing the expression of a cellular protein may also encode an RNA molecule, e.g. antisense RNA or ribozyme, which will inhibit an undesired cellular activity, e.g. in a virus-infected cell or tumor cell. Additionally, the nucleic acid can carry a label (e.g., radioactive label, fluorescent label or colorimetric label) for the purpose of providing clinical diagnosis relating to the presence or absence of complementary nucleic acids. Accordingly, the nucleic acids, or nucleotide polymers, can be polymers of nucleic acids including genomic DNA, cDNA, mRNA or oligonucleotides containing nucleic acid analogs, for example, the antisense derivatives described in a review by Stein, et al., Science 261:1004–1011 (1993) and in U.S. Pat. Nos. 5,264,423 and 5,276,019, the disclosures of which are incorporated herein by reference. Still further, the nucleic acids may encode transcriptional and translational regulatory sequences including promoter sequences and enhancer sequences.

The nucleotide polymers can be single-stranded DNA or RNA, or double-stranded DNA or DNA-RNA hybrids. Examples of double-stranded DNA include structural genes including control and termination regions, and self-replicating systems such as plasmid DNA.

Single-stranded nucleic acids include antisense oligonucleotides (complementary to DNA and RNA), ribozymes and triplex-forming oligonucleotides. In order to increase stability, some single-stranded nucleic acids will preferably have some or all of the nucleotide linkages substituted with stable, non-phosphodiester linkages, including, for example, phosphorothioate, phosphorodithioate, phosphoroselenate, or O-alkyl phosphotriester linkages.

The nucleic acids used in the present invention will also include those nucleic acids in which modifications have been made in one or more sugar moieties and/or in one or more of the pyrimidine or purine bases. Examples of sugar modifications include replacement of one or more hydroxyl groups with halogens, alkyl groups, amines, azido groups or functionalized as ethers or esters. Additionally, the entire sugar may be replaced with sterically and electronically similar structures, including aza-sugars and carbocyclic sugar analogs. Modifications in the purine or pyrimidine base moiety include, for example, alkylated purines and pyrimidines, acylated purines or pyrimidines, or other heterocyclic substitutes known to those of skill in the art.

Multiple genetic sequences can be also be used in the present methods. Thus, the sequences for different proteins may be located on the same or separate plasmids. The gene of interest will be linked to appropriate regulatory elements to provide constitutive or inducible expression and/or tissue specific expression. Additional elements such as antibiotic-sensitive or nutrient-sensitive regions, may be included as required. Non-encoding sequences may also be present for various purposes including, for example, regulatory elements to achieve appropriate expression or replication in host cells, or to provide convenient cloning sites.

The nucleic acids used in the present invention can be isolated from natural sources, obtained from such sources as ATCC or GenBank libraries or prepared by synthetic methods. Typically, the nucleic acids will be plasmid DNA, which can be grown and purified in large quantities from bacterial cells.

Synthetic nucleic acids can be prepared by a variety of solution or solid phase methods. Generally, solid phase synthesis is preferred. Detailed descriptions of the procedures for solid phase synthesis of nucleic acids by phosphite-triester, phosphotriester, and H-phosphonate chemistries are widely available. See, for example, Itakura, U.S. Pat. No. 4,401,796; Caruthers, et al., U.S. Pat. Nos. 4,458,066 and 4,500,707; Beaucage, et al., *Tetrahedron Lett.*, 22:1859–1862 (1981); Matteucci, et al., *J. Am. Chem. Soc.*, 103:3185–3191 (1981); Caruthers, et al., *Genetic Engineering*, 4:1–17 (1982); Jones, chapter 2, Atkinson, et al., chapter 3, and Sproat, et al., chapter 4, in *Oligonucleotide Synthesis: A Practical Approach*, Gait (ed.), IRL Press, Washington D.C. (1984); Froehler, et al., *Tetrahedron Lett.*, 27:469–472 (1986); Froehler, et al., *Nucleic Acids Res.*, 14:5399–5407 (1986); Sinha, et al. *Tetrahedron Lett.*, 24:5843–5846 (1983); and Sinha, et al., *Nucl. Acids Res.*, 12:4539–4557 (1984) which are incorporated herein by reference.

The compositions in this aspect of the invention can be in the form of liposome-encapsulated nucleic acids, lipid-bilayer coated nucleic acids, or complexes formed between lipids and nucleic acids such as plasmids.

Preparation of Lipid-Nucleic Acid Compositions

Various lipid-nucleic acid compositions, wherein the lipid portion is typically in the form of liposomes, can be prepared using methods well known in the art. Still other compositions are contemplated by the present invention such as those which are described as lipid particles in WO 96/40964, the disclosure of which is incorporated herein by reference.

For those compositions in which the lipid portion is in the form of liposomes, the lipid vesicle can be prepared by standard methods such as those described above. The resulting liposomes are mixed with a nucleic acid solution with constant agitation to form the cationic lipid-nucleic acid transfection complexes. The preferred size will vary depending on use. For example, smaller transfection complexes are preferred for aerosol administration, thereby reducing shear caused by the aerosolization process. Preferred transfection complex size for aerosol administration is less than 5000 nm, most preferably from 50 to 300 nm. Preferred transfection complex size for intravenous administration is from 50 to 5000 nm, most preferably from 100 to 400 nm. Cationic lipid-nucleic acid transfection complexes can be prepared in various formulations depending on the target cells to be transfected. See, e.g., WO 96/40962 and WO 96/40963. Neutral lipids used in these compositions can be substituted and evaluated for concentration, DNA-lipid ratio, etc. For example, if DLPE is substituted for cholesterol, resulting in changes in the physical characteristics of the lipid carrier, it is preferred that additional formulations be tested empirically to obtain optimal results. While a range of lipid-nucleic acid complex formulations will be effective in cell transfection, optimum conditions are determined empirically in the desired experimental system. Lipid carrier compositions may be evaluated by their ability to deliver a reporter gene (e.g. CAT which encodes chloramphenicol acetyltransferase, luciferase, or β-galactosidase) in vitro, or in vivo to a given tissue in an animal, such as a mouse.

For in vitro transfections, the various combinations are tested for their ability to transfect target cells using standard molecular biology techniques to determine DNA uptake, RNA and/or protein production. Typically, in vitro cell transfection involves mixing nucleic acid and lipid, in cell culture media, and allowing the lipid-nucleic acid transfection complexes to form for about 10 to 15 minutes at room temperature. The transfection complexes are added to the cells and incubated at 37° C. for about four hours. The complex-containing media is removed and replaced with fresh media, and the cells incubated for an additional 24 to 48 hours.

In vivo, particular cells can be preferentially transfected by the use of particular cationic lipids for preparation of the lipid carriers, or by altering the cationic lipid-nucleic acid formulation to preferentially transfect the desired cell types (WO 96/40962). Thus, for example, in circumstances where a negatively charged complex is desired, relatively less cationic lipid will be complexed to the nucleic acid resulting in a higher nucleic acid: cationic lipid ratio. Conversely, in circumstances where a positively charged complex is desired, relatively more cationic lipid will be complexed with the nucleic acid, resulting in a lower nucleic acid: cationic lipid ratio. To avoid precipitation, which generally occurs around charge neutrality, net positively charged complexes are generally prepared by adding nucleic acid to the liposomes, and net negatively charged complexes are prepared by adding liposomes to the nucleic acid, in either case with constant agitation.

The lipid mixtures are complexed with DNA in different ratios depending on the target cell type, generally ranging from about 6:1 to 1:20 μg DNA:nmole cationic lipid. For transfection of airway epithelial cells, e.g., via aerosol, intratracheal or intranasal administration, net negatively charged complexes are preferred. Thus, preferred DNA:cationic lipid ratios are from about 10:1 to about 1:20, preferably about 3:1. For intravenous administration, preferred DNA:cationic lipid ratios range from about 1:3.5 to about 1:20 μg DNA:nmole cationic lipid, most preferably, about 1:6 to about 1:15 μg DNA:nmole cationic lipid. Additional parameters such as nucleic acid concentration, buffer type and concentration, etc., will have an effect on transfection efficiency, and can be optimized by routine experimentation by a person of ordinary skill in the art. Preferred conditions are described in the Examples that follow.

Non-lipid material, (such as biological molecules being delivered to an animal or plant cell or target-specific moieties) can be conjugated to the lipid carriers through a linking group to one or more hydrophobic groups, e.g., using alkyl chains containing from about 12 to 20 carbon atoms, either prior or subsequent to vesicle formation. Various linking groups can be used for joining the lipid chains to the compound. Functionalities of particular interest include thioethers, disulfides, carboxamides, alkylamines, ethers, and the like, used individually or in combination. The particular manner of linking the compound to a lipid group is not a critical part of this invention, as the literature provides a great variety of such methods. Alternatively, some compounds will have hydrophobic regions or domains which will allow their association with the lipid mixture without covalent linking to one or more lipid groups.

Administration of Lipid-nucleic Acid Compositions to a Host

Following formation of the lipid-nucleic acid compositions, the compositions (or complexes) can be contacted with the cells to be transfected. Contact between the cells and the lipid-nucleic acid complexes, when carried out in vitro, will take place in a biologically compatible medium. The concentration of complexes can vary widely depending on the particular application, but is generally between about 1 μmol and about 10 mmol. Treatment of the cells with the lipid-nucleic acid complexes will generally be carried out at physiological temperatures (about 37° C.) for periods of time of from about 1 to 48 hours, preferably of from about 2 to 4 hours. For in vitro applications, the delivery of nucleic acids can be to any cell grown in culture, including primary cell and immortalized cell lines, whether of plant or animal origin, vertebrate or invertebrate, and of any tissue or type. In preferred embodiments, the cells will be animal cells, more preferably mammalian cells, and most preferably human cells.

In one group of preferred in vitro embodiments, a lipid-nucleic acid composition suspension is added to 60–80% confluent plated cells. The concentration of the suspension added to the cells is preferably of from about 0.01 to 0.2 μg/mL, more preferably about 0.1 μg/mL.

Typical applications include using well known transfection procedures to provide intracellular delivery of DNA or mRNA sequences which code for therapeutically useful polypeptides. However, the compositions can also be used for the delivery of the expressed gene product or protein itself In this manner, therapy is provided for genetic diseases by supplying deficient or absent gene products (i.e., for Duchenne's dystrophy, see, Kunkel, et al., *Brit. Med. Bull.* 45(3):630–643 (1989), and for cystic fibrosis, see, Goodfellow, *Nature* 341:102–103 (1989)). Other uses for the compositions of the present invention include introduction of antisense oligonucleotides in cells (see, Bennett, et al., *Mol. Pharm.* 41:1023–1033 (1992)).

The compositions of the present invention can also be used for the transfection of cells in vivo, using methods which are known to those of skill in the art. In particular, Zhu, et al., *Science* 261:209–211 (1993), incorporated herein by reference, describes the intravenous delivery of cytomegalovirus (CMV)-chloramphenicol acetyltransferase (CAT) expression plasmid using DOTMA-DOPE complexes. Hyde, et al., *Nature* 362:250–256 (1993), incorporated herein by reference, describes the delivery of the cystic fibrosis transmembrane conductance regulator (CFTR) gene to epithelia of the airway and to alveoli in the lung of mice, using liposomes.

In one group of embodiments, the in vivo administration of the pharmaceutical compositions is carried out parenterally, e.g., intraarticularly, intravenously, intraperitoneally, subcutaneously, or intramuscularly. More preferably, the pharmaceutical compositions are administered intravenously for delivery to vascular endothelial cells, by intraperitoneal injection for delivery to peritoneal macrophages or cells lining the peritoneal cavity, or by intramuscular or subcutaneous injection for delivery to antigen-presenting cells for purposes of eliciting an immune response. For example, see Stadler, et al., U.S. Pat. No. 5,286,634, which is incorporated herein by reference. Intracellular nucleic acid delivery has also been discussed in Straubringer, et al., METHODS IN ENZYMOLOGY, Academic Press, New York. 101:512–527 (1983); Mannino, et al., *Biotechniques* 6:682–690 (1988); Nicolau, et al., *Crit. Rev. Ther. Drug Carrier Syst.* 6:239–271 (1989), and Behr, *Acc. Chem. Res.* 26:274–278 (1993).

In other embodiments, the pharmaceutical preparations described herein may be contacted with the target tissue by direct application of the preparation to the tissue. The application may be made by topical, "open" or "closed" procedures. By "topical", it is meant the direct application of the pharmaceutical preparation to a tissue exposed to the environment, such as the skin, oropharynx, external auditory canal, and the like. "Open" procedures are those procedures include incising the skin of a patient and directly visualizing the underlying tissue to which the pharmaceutical preparations are applied. This is generally accomplished by a surgical procedure, such as a thoracotomy to access the lungs, abdominal laparotomy to access abdominal viscera, or other direct surgical approach to the target tissue, for example, heart tissue and/or associated vasculature may be transfected with a gene of interest in conjunction with heart surgery, as an adjunct therapy. "Closed" procedures are invasive procedures in which the internal target tissues are not directly visualized, but accessed via inserting instruments through small wounds in the skin. For example, the preparations may be administered to the peritoneum by needle lavage or to the vasculature using a balloon catheter. Likewise, the pharmaceutical preparations may be administered to the meninges or spinal cord by infusion during a lumbar puncture followed by appropriate positioning of the patient as commonly practiced for spinal anesthesia or metrazamide imaging of the spinal cord. Alternatively, the preparations may be administered through endoscopic devices.

In yet other embodiments, the lipid-nucleic acid complexes can be administered in an aerosol inhaled into the lungs (see U.S. Pat. No. 5,641,662). For a general review of applicable techniques, see, Culver, HUMAN GENE THERAPY, Mary Ann Liebert, Inc., Publishers, New York. pp.70–71 (1994).

The methods of the present invention may be practiced in a variety of hosts. Preferred hosts include mammalian species, such as humans, non-human primates, dogs, cats, cattle, horses, sheep, and the like.

The invention will be better understood in light of the following specific examples, which are merely illustrative and should not be construed as limiting the invention in any respect, as will be evident to those skilled in the art.

EXAMPLES

All of the reagents were purchased from Aldrich Chemical Company (Milwaukee, Wis., USA), except oleyl alcohol, which was obtained from Nu-Chek-Prep, Inc. (Elysian, Minn., USA). All solvents were purchased from Fisher Scientific.

Example 1

This example illustrates the preparation of compounds corresponding to Formula I. Four families of compounds corresponding to Formula I have been synthesized. The synthesis of each of these four families is detailed in Examples 1.1 to 1.4.

Scheme 1

1.1 Synthesis of compounds of family 1

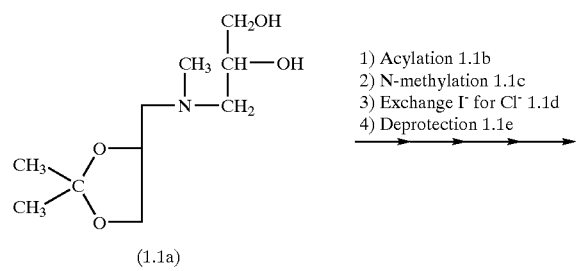

(1.1a)

1) Acylation 1.1b
2) N-methylation 1.1c
3) Exchange I⁻ for Cl⁻ 1.1d
4) Deprotection 1.1e

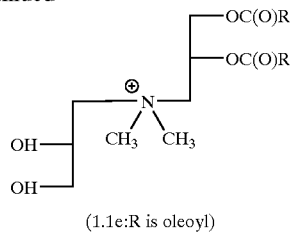

(1.1e:R is oleoyl)

1.1a Synthesis of the Basic Structure 1,2-Isopropylidene-rac-propanediol-(1,2)-3-mesylate (MW 210.24; 77 g, 0.35 mol) was dissolved in 33% N-methylamine in ethanol (400 mL) and heated in a closed vessel at 50° C. for 24 hrs. The reaction was complete by TLC:CHCl$_3$/acetone 10:1); starting mesylate R$_f$~0.7; product [1.2-isopropylidene-propanediol-1.2-N-(methyl)-amine] R$_f$~10.1. The starting material was almost completely converted to the product. The solvent was removed from the reaction mixture and the residue was shaken with a mixture of CHCl$_3$/CH$_3$OH/10% sodium carbonate in water (500:500:500). After phase separation, the lower phase is removed and the solvent evaporated therefrom resulting in 35 g of product (yield ~70%). The oily residue (MW 145.20; 35 g, 0.24 mol) was dissolved in toluene (150 mL) and heated to reflux. Glycidol (MW 74.08; 22 g, 0.30 mol) dissolved in toluene (100 mL) was added dropwise and the reaction mixture was refluxed for 60 min. The reaction was followed by TLC:CHCl$_3$/CH$_3$OH (4:1); starting amine R$_f$=0.4; glycidol R$_f$=0.8; Product R$_f$=0.55. The solvent was removed from the reaction mixture and the oily residue was dried at 1 Torr for 12 hrs. The product (MW 219.28) is obtained in 96% yield (0.23 mol).

1.1b Acylation of the Basic Structure With Oleoyl Chloride

Amine from 1.1a (MW 219.28; 16.4 g, 0.075 mol), triethylamine (MW 101.19; 15.2 g, 0.15 mol) and (N,N-dimethyl)-aminopyridine (MW 122.17; 2.4 g, 0.02 mol) were dissolved in CHCl$_3$ (300 mL). Under continuous stirring at 20° C., acylation was performed utilizing the dropwise addition of oleoyl chloride (MW 300.91; 45 g, 0.15 mol) in CHCl$_3$ (200 mL). The temperature of the reaction mixture was maintained below 35° C. After the addition of the acyl chloride was complete, stirring was continued for 30 min. The reaction was complete as demonstrated by TLC:CHCl$_3$/CH$_3$OH (4:1); starting material, R$_f$=0.55; Product, R$_f$=0.95. CH$_3$OH (400 mL) and 0.9% saline (400 mL) were added to the reaction mixture under continuous stirring. Stirring was stopped and the phases were allowed to separate. The CHCl$_3$ phase was removed and evaporated to dryness affording 55 g of the acylated intermediate amine (MW 748.18) TLC:CHCl$_3$/CH$_3$ OH (4:1); R$_f$=0.95:CHCl$_3$/ethyl acetate (1:1); R$_f$=0.70).

1.1c N-Methylation of the Acylated Amine

The acylated amine (MW 792.23; 39.6, 0.05 mol) was dissolved in a mixture of CHCl$_3$ (300 mL) and CH$_3$I (MW 141.94; 14.29 g, 0.10 mol). The reaction mixture was maintained at 50° C. for 60 min. TLC indicated that the methylation was complete. TLC:CHCl$_3$/ethyl acetate (1:1); starting material, R$_f$=0.65; product, R$_f$=0.0. The product had an R$_f$=0.30 in CHCl$_3$/CH$_3$OH/acetic acid/water (300:60:20:5).

1.1d Exchange of Chloride for Iodide

The chloroform phase containing the permethylated product was thoroughly shaken with a solution of NaCl (75 g) in H$_2$O (300 mL) and CH$_3$OH (300 mL) and the organic and aqueous phases were allowed to separate. The aqueous layer was removed and the organic layer was treated four more times with the NaCl solution. The replacement of Cl$^-$ for I$^-$ was confirmed by an iodide test using HIO$_4$. The solvent was removed by evaporation affording 37 g of a viscous oil (MW 798.67). TLC:CHCl$_3$/CH$_3$OH/acetic acid/H$_2$O (300:60:20:5); R$_f$=0.15.

1.1e Deprotection

The chloride from step 1.1d, as a viscous oil (MW 842.72; 16.8 g, 0.02 mol), was dissolved in THF (100 mL) and 4 N HCl (20 mL). The reaction was monitored by TLC and was complete after 20 min at 45° C. TLC:CHCl$_3$/CH$_3$OH/acetic acid/water (300:60:20:5); starting material, R$_f$=0.15; product, R$_f$=0.05. The oily residue was purified by column chromatography with the solvent system CHCl$_3$/CH$_3$OH in the proportions shown in Table 1, below. The product (8 g) is a wax-like material (MW 792.93).

TABLE 1

| CHCl$_3$:CH$_3$OH | Use |
|---|---|
| 20:1 | to prepare the column |
| 10:1 | to remove byproducts |
| 7:3 | to elute the product |

1.2 Synthesis of Compounds of Family 2

This example details the synthesis of representative compounds of family 2. The synthesis was accomplished by a procedure exemplified in Scheme 2.

Scheme 2

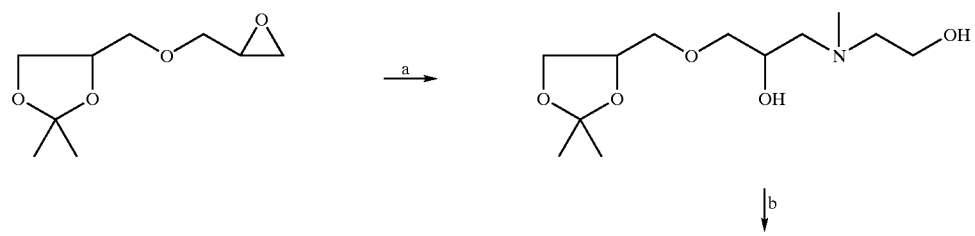

-continued

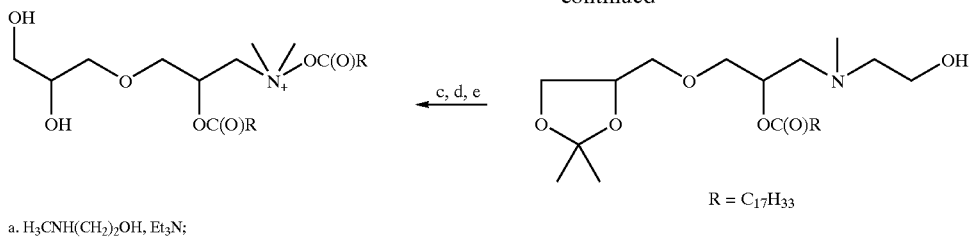

R = C₁₇H₃₃ a. H₃CNH(CH₂)₂OH, Et₃N;
b. ClC(O)C₁₇H₃₃, Et₃N, DMAP;
c. CH₃I;
d. Ion exchange (I⁻ for Cl⁻);
e. HCl, THF 1.2a Synthesis of the Basic Structure N-methylethanolamine (MW 75.11; 45 g, 0.6 mol) was dissolved in toluene (100 mL). The solution was heated to reflux and 1,2-isopropylidene-glycero-3-glycidol (MW 188.22; 86 g, 0.46 mol) in toluene (100 mL) was added dropwise over 1 hr. After 2 additional hours heating under reflux, the reaction was complete by TLC:ether/pentane (1:1); starting material (glycidol), $R_f$=0.6; product, $R_f$=0.1. The reaction mixture was freed from solvent by rotary evaporation. The oily residue was purified by column chromatography with the solvent system CHCl₃/CH₃OH in the proportions shown in Table 1, above.

Solvent was removed from the product fractions and the oily residue, 71 g was used without further purification in the next (acylation) step. The product (MW 263.33) was obtained in 59% yield.

1.2b Acylation of the Basic Structure

The amine from step 1.2a, above (MW 263.33; 0.075 mol—16.8 g), triethylamine (MW 101.19; 15.2 g, 0.15 mol) and N,N-dimethylaminopyridine (MW 122.17; 2.4 g, 0.02 mol) were dissolved in CHCl₃ (300 mL). Under continuous stirring at 20° C., acylation with oleoyl chloride (MW 300.91; 45 g, 0.15 mol) dissolved in CHCl₃ (200 mL) was performed by dropwise addition. The temperature of the reaction mixture was maintained below 35° C. After the addition of the oleoylchloride, stirring was continued at 35° C. for 30 min. The reaction was complete as demonstrated by TLC:CHCl₃/ethyl acetate (1:1); starting material (amine), $R_f$=0.05; product, $R_f$=0.65.

Methanol (400 mL) was added to the reaction mixture followed by 0.9% saline (400 mL). The mixture was transferred to a separatory funnel and thoroughly shaken. After phase separation, the lower CHCl₃-phase was separated and the solvent was evaporated. 58 g of the acylated intermediate amine were isolated (MW 792.23). TLC:CHCl₃/ethyl acetate (1:1); $R_f$=0.65.

1.2c N-Methylation of the Acylated Amine

The acylated amine from step 1.2b (MW 748.18; 37.5 g, 0.05 mol) was dissolved in CHCl₃ (300 mL) and CH₃I (MW 141.94; 14.2 g, 0.10 mol) was added. After 60 min. at 50° C. in a water bath, the methylation was complete. TLC:CHCl₃/ethyl ether (1:1); starting material, $R_f$=0.70; product, $R_f$=0.0. When submitted to TLC using CHCl₃/CH₃OH/acetic acid/water (300:60:20:5), the product, 1,2-dioleoylpropandiol-(1, 2)-(N,N,N-trimethyl)amonium iodide, had an $R_f$=0.35.

1.2d Exchange of Chloride for Iodide

The chloroform phase with the permethylated product was thoroughly shaken with a solution of NaCl (75 g) in H₂O (300 mL) and CH₃OH (300 mL). After phase separation, the lower phase was treated an additional four times with sodium chloride. According to TLC and according to an iodide test with HIO₄ (Iodine formation), the material was completely transformed to the chloride salt. TLC:CHCl₃/CH₃OH/acetic acid/H₂O (300:60:20:5); $R_f$=0.20. The CHCl₃-phase was freed from solvent, resulting in 35 g of a viscous oil.

1.2e Deprotection

The oily residue from step 1.2d (MW 798.67; 16 g, 0.02 mol) was dissolved in THF (100 mL) and 4 N HCl (20 mL). After 20 min at 45° C., the cleavage of the isopropylidene protecting group was completed. The reaction mixture was extracted with diisopropylether (300 mL), 2-propanol (50 mL) and 5% NaCl (300 mL). After thoroughly shaking, phase separation occurs. The upper diisopropylether phase contains the product. This phase was evaporated, hexane (300 mL) was added to the residue the mixture was again evaporated. The viscous residue (12 g) was dissolved in CHCl₃/ 2-propanol/H₂O (800:200:2). Chromatography on 120 g Silica gel (Merck) was performed with the solvent systems displayed in Table 2, below.

TABLE 2

| solvent system | CHCl₃ | 2-Propanol | CH₃OH | H₂O |
| --- | --- | --- | --- | --- |
| A | 800 | 150 | 50 | 2 |
| B | 700 | 200 | 200 | 3 |
| C | 600 | — | 400 | 3 |

System C eluted the product. After removing the solvent 9 g (MW 758.60) of the desired product were isolated as a very viscous material which does not crystallize; TLC:CHCl₃/CH₃OH/acetic acid/H₂O (300:60:20:5); $R_f$=0.1.

1.3 Synthesis of Family 3

A third family of compounds according to Formula I can be prepared by the series of reactions outlined in Scheme 3.

Scheme 3

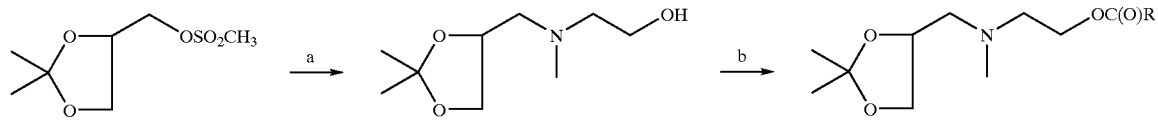

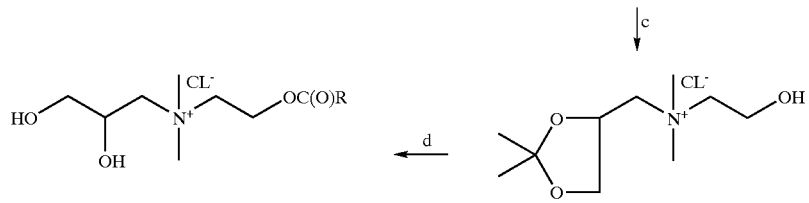

a. CH₃NH(CH₂)₂OH, reflux, 2 h;
b. RC(O)Cl, Et₃N, DMAP;
c. CH₃I, CH₃Cl (II) Ion exchange;
d. HCl/THF

1.3a Synthesis of the Basic Structure 1,2-isopropylidene-glycero-3-mesylate (MW 210.2:—210 g, 1 mol) was dissolved in 1-propanol (600 mL) and N-methylethanolamine (MW 75.1; 150.2 g, 2 mol) was added. Following the addition of the amine, the reaction mixture is heated to reflux and maintained for 2 h. At the end of this time, TLC indicated that the starting mesylate was completely consumed. TLC:CHCl₃/CH₃OH (2:1); $R_f$=0.9. The solvent was removed by evaporation and the residue was dissolved in THF (300 mL) and cooled to 4° C. The crystals which formed were isolated and the filtrate was evaporated to dryness and distilled. The product (MW 189.25) was obtained in 75% yield (142 g, 0.75 mol); bp $10^{-3}$ bar, 84–86° C.; TLC:CHCl₃/CH₃OH (2:1); $R_f$=0.6.

1.3b Acylation of Basic Structure With Erucoyl Chloride

The acylation was performed by a method analogous to those described above. Briefly, the amine from step 1.3a (18.9 g, 0.1 mol), triethylamine (MW 101.19; 10.1 g, 0.1 mol) and N,N-dimethylaminopyridine (MW 122.17; 1.6 g, 0.013 mol) were dissolved in CH₃Cl (200 mL). Under continuous stirring at 20° C., erucoyl chloride (MW 357.0; 35.7 g, 0.1 mol) in CH₃Cl (100 mL) was added dropwise. The addition was conducted such that the reaction temperature remained below 35° C. After the addition was complete, stirring was continued for 30 min at less than 35° C. At the end of this time, TLC indicated that the reaction was complete. TLC:CHCl₃/ethyl acetate (1:1); $R_f$=0.5.

CH₃OH (300 mL) was added to the reaction mixture, followed by 2% NaCl (300 mL). The solution was thoroughly shaken and the phases allowed to separate. The lower phase was collected and the solvent was removed by evaporation. The crude product (55 g) was purified by chromatography on silica gel (200 g, Merck) using the conditions in Table 3. The column was packed with solvent A and solvents B and C were used to elute the product yielding 42 g of pure material (MW 509.8; 0.082 mol, 82% yield).

TABLE 3

| Solvent System | A | B | C |
|---|---|---|---|
| cyclohexane | 800 | 700 | 600 |
| chloroform | 200 | 200 | 200 |
| ethyl acetate | 20 | 100 | 200 |

1.3c N-Methylation of the Acylated Amine

The acylated amine from step 1.3b (MW 509.8; 40.8 g, 0.08 mol) was dissolved in CHCl₃ (200 mL) and CH₃I (MW 141.94; 42 g, 0.3 mol) was added. The reaction mixture was heated to 50° C. for 60 min. Complete methylation was confirmed by TLC:CHCl₃/ethyl acetate (1:1); starting material, $R_f$=0.70; product, $R_f$=0.0. The product, N-erucoylhydroxyethyl-N-1,2-isopropylidenedihydroxypropyl-N,N-dimethylammonium iodide, had an $R_f$=0.25 in CHCl₃/CH₃OH/acetic acid/H₂O (300:60:20:5).

1.3d Exchange of Chloride for Iodide

The procedure for the ion exchange is substantially similar to that described above. Following the ion exchange, the iodide has been quantitatively exchanged with chloride as demonstrated by HIO₄. The solvent is removed by evaporation leaving a viscous oil. TLC:CHCl₃/CH₃OH/acetic acid/H₂O (300:60:20:5); $R_f$=0.10.

1.3e Deprotection

The oily residue from step 1.3d (MW 560.30; 40 g, 0.071 mol) was dissolved in THF (200 mL) and 2N HCl (20 mL). The mixture was stirred for 30 min at 45° C. to 50° C. until the hydrolysis of the isopropylidene group was complete as demonstrated by TLC. TLC:CHCl₃/CH₃OH/acetic acid/H₂O (300:60:20:5); $R_f$=0.10. The product was isolated by extracting the reaction mixture with CHCl₃ (400 mL), CH₃OH (400 mL) and 5% NaCl (400 mL). The lower phase is removed and evaporated to dryness. The residue was dissolved in methylethyl ketone (500 mL) at 60° C. and subsequently cooled to 18° C., at which point crystals formed. The crystals were isolated via filtration, washed with pentane and dried under vacuum (10 mbar, 20° C.), yielding 20 g (MW 520.33; 0.39 mol; 39% yield) of the desired product.

1.4 Synthesis of Compounds of Family 4

A fourth family of compounds according to Formula I can be prepared by the series of reactions outlined in Scheme 4.

Scheme 4

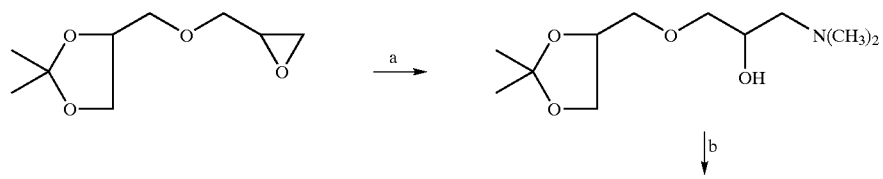

-continued

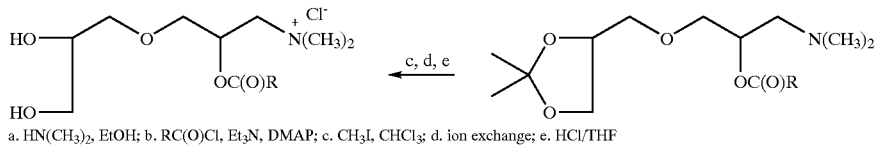

a. HN(CH₃)₂, EtOH; b. RC(O)Cl, Et₃N, DMAP; c. CH₃I, CHCl₃; d. ion exchange; e. HCl/THF 1.4a Synthesis of the Basic Structure 1,2-isopropylideneglycero-3-glycidol (MW 188.22; 47.1 g, 0.25 mol) was dissolved in 5.6 M dimethylamine in ethanol (100 mL, ~0.56 mol). The solution was kept at 30° C. to 40° C. for 2 h. The solvent was removed by evaporation and the residue was purified by chromatography on silica gel (Merck, 200 g). The yield of the product, N-(1,2-isopropylidene)-dihydroxypropyl-N-dihydroxypropyl-N-methylamine, was 30 g (0.129 mol, 52%). TLC:CHCl₃/CH₃OH (4:1); $R_f$=0.3.

1.4b Acylation of the Basic Structure With Erucoyl Chloride

The amine form step 1.4a (MW 233.31; 23.3 g, 0.1 mol), triethylamine (MW 101.19; 10.1 g, 0.1 mol) and N,N-dimethylaminopyridine (MW 122.17; 1.2 g, 0.01 mol) were dissolved in CHCl₃ (200 mL). Erucoyl chloride (MW 357.02; 35.7 g, 0.1 mol) was dissolved in CHCl₃ (100 mL) and added dropwise at 20° C. under continuous stirring while the reaction temperature was maintained below 35° C. After the addition was complete, the mixture was stirred for an additional 30 min. CH₃OH (300 mL) and 2% NaCl (300 mL) were added to the reaction mixture. The reaction mixture was shaken thoroughly and the phases were allowed to separate. The lower phase was removed and evaporated to dryness affording an oily residue (50 g). Purification of the residue by chromatography on silica gel was performed as described in 1.3b, above. The product was obtained in 60% yield (MW 513.80; 31 g, 0.06 mol). TLC:CHCl₃/CH₃OH (9:1); $R_f$=0.6.

1.4c N-Methylation of the Acylated Amine

The acylated amine from step 1.4b (MW 513.80; 31 g, 0.06 mol) was dissolved in CHCl₃ (300 mL) and CH₃I (MW 141.94; 28 g, 0.20 mol). After 60 min at 50° C., the methylation was complete. TLC:CHCl₃/CH₃OH/acetic acid/H₂O (600:60:20:5); $R_f$=0.15.

1.4d Exchange of Chloride for Iodide

The CHCl₃ containing the methylated product from 1.4c was submitted to ion exchange using substantially the same conditions as described above for ion exchange. The solvent is subsequently removed and the product is isolated as an oil.

1.4e Deprotection

The oil from step 1.4d (MW 604.35; 36.2 g, 0.06 mol) was dissolved in THF (200 mL) and 2N HCl (20 mL). After 30 min at 45° C. to 50° C., the hydrolysis of the isopropylidene protecting group was judged complete by TLC. TLC:CHCl₃/CH₃OH/acetic acid/H₂O (300:60:20:5); starting material, $R_f$=0.10; product, $R_f$=0.05. The product was extracted with CHCl₃ (400 mL), CH₃OH (400 mL) and 5% NaCl (400 mL). The lower phase was separated and the solvent removed by evaporation. The residue was dissolved in methylethyl ketone (500 mL) at 60° C. then cooled to −20° C. The product separated out as white crystals which were collected by filtration and dried under vacuum (10 mbar, 20° C.). The yield was 44% (MW 564.29, 25 g, 0.044 mol).

Lipid Synthesis 3-(Dimethylamino)-1,2-propanediol was treated with sodium hydride followed by alkylation with alkyl methanesulfonate to give ether intermediate MBN305A. Further nucleophilic substitution of MBN305A with 1-chloro-2,3-dihydroxypropane gave the new lipid MBN305 (Scheme 5).

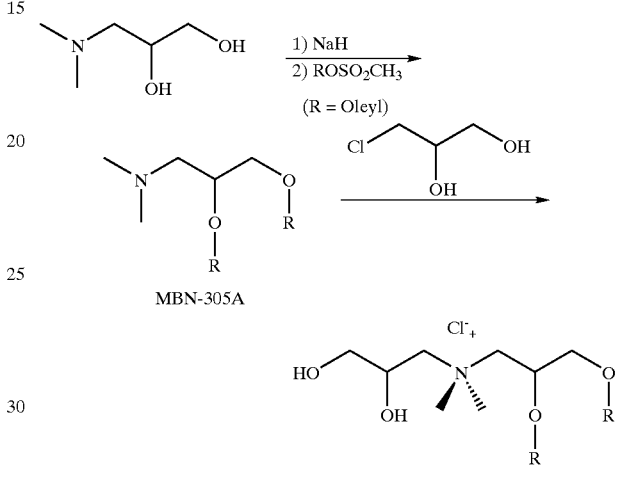

N,N-Dimethyl-2,3-dioleyloxypropane (MBN305A)

To a stirred suspension of NaOH (0.96 g, 60%, 24 mmol) in THF (40 mL), 3-(dimethylamino)-1,2-propanediol (1.2 g, 10 mmol) was added at room temperature. After the reaction mixture was refluxed for 3 h, oleyl methanesulfonate was added. The reaction mixture was then heated under reflux for 3 days and then cooled to room temperature. Water (50 mL) was added and the mixture was extracted with methylene chloride (4×25 mL). The methylene chloride phase was washed with water (30 mL) and sodium chloride solution (30 mL), dried over magnesium sulfate, evaporated under reduced pressure. The residue was purified on silica gel column using (MeOH/CH₂Cl₂, 0–2%) as eluant to yield 3.4 (54.5%) of MBN305A. ¹H NMR (CDCl₃): δ 0.88 (t, J=7, 6H), 1.25 (m, 44H), 1.58 (m, 4H), 2.02 (m, 8H), 2.16 (s, 6H), 2.22 (m, 2H), H), 5.36 (m, 4H).

N,N-Dimethyl-N-(2,3-dihydroxypropanylo-N-(2,3-dioleyloxypropanyl)amonium Chloride (MBN-305)

A mixture of MBN305A (1.5 g, 2.42 mmol) and 3-chloro-1,2-propanediol (1.65 g, 14.54 mmol) was stirred at 105–110° C. for 20 h. The reaction mixture was purified by a silica gel column using MeOH/CH₂Cl₂ (0–2%) as the eluant to give 0.67 g of MBN305 (38.0%). ¹H NMR (CDCl₃): δ 0.89 (t, J=7,6H), 1.28 (m, 44H), 1.56 (m, 4H), 3.0–4.0 (m, 18H), 4.10 (m, 1H), 4.45 (m, 1H), 5.36 (m, 4H). Anal. Calcd for C₄₄H₈₈NO₄Cl.1.3H₂O: C, 70.12; H, 12.04; N, 1.86; Cl, 4.71. Found: C, 70.23; H, 12.18; N, 1.87; Cl, 4.71.

Example 2

This example illustrates the synthesis of compounds according to Formula II. One set of reaction conditions which can be used to produce the compounds of Formula II is generalized in Scheme 6. This basic synthetic format was used to synthesize each of the compounds detailed in Example 2.

An example of the synthesis of specific compounds belonging to the first family of compounds corresponding to Formula I is described in Scheme 6, below.

Scheme 6

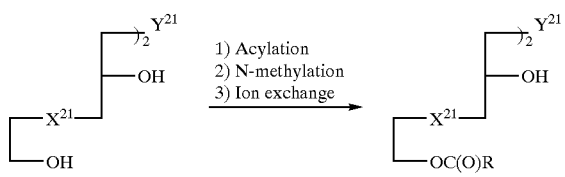

2.1 Synthesis of Compounds Corresponding to Formula 2

A family of compounds according to Formula II can be prepared by the procedure outlined in Scheme 7.

Scheme 7

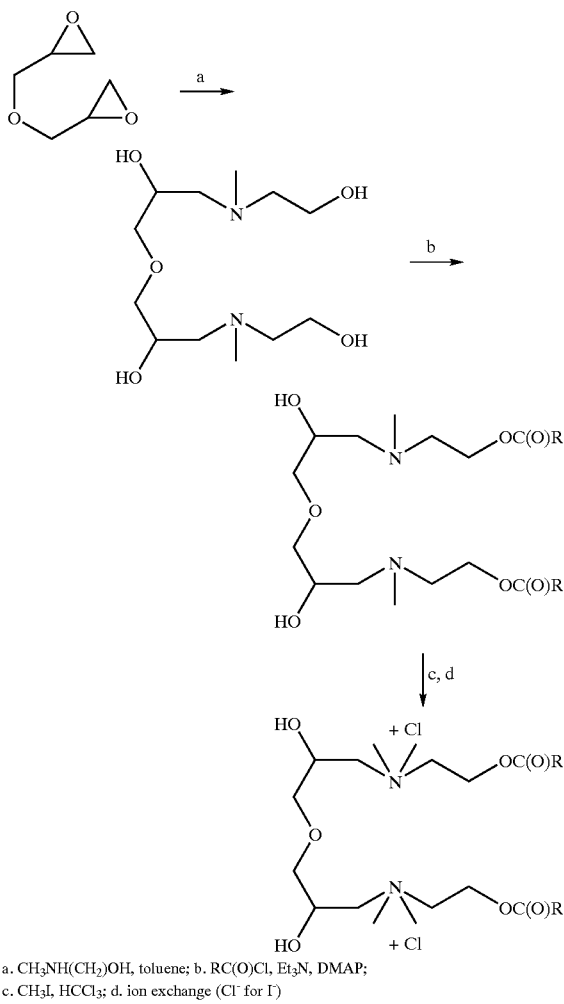

a. $CH_3NH(CH_2)OH$, toluene; b. $RC(O)Cl$, $Et_3N$, DMAP;
c. $CH_3I$, $HCCl_3$; d. ion exchange (Cl- for I-)

2.1a Synthesis of the Basic Structure

N-Methylethanolamine (MW 75.11; 75 g, 1 mol) and glycidoglycidol (MW 130.14; 52 g, 0.4 mol) in toluene (300 mL) were heated under reflux for 1 hr. The solvent was removed from the reaction mixture and an oily residue (210 g) was purified chromatography using the solvent systems in Table 4.

TABLE 4

| Solvent System | A | B | C | D |
|---|---|---|---|---|
| $CHCl_3$ | 100 | 65 | 65 | 50 |
| $CH_3OH$ | 15 | 15 | 30 | 50 |
| ammonia 12.5% | 1 | 1 | 3 | 5 |

The product eluted with solvent systems C and D resulting in a yield of 110 g (49%, MW 280.36). TLC:solvent C; $R_f$=0.25.

2.1b Acylation of the Basic Structure

The amine from step 2.1a (MW 280.36; 14 g, 0.05 mol), triethylamine (MW 101.19; 10.1 g, 0.1 mol) and N,N-dimethylaminopyridine (MW 122.17; 1.6 g, 0.013 mol) were dissolved in $CHCl_3$ (300 mL) under continuous stirring. Myristoyl chloride (MW 246.82; 24.7 g, 0.1 mol) dissolved in $CHCl_3$ (10 mL) was added dropwise. The temperature of the reaction mixture was carefully controlled using an ice bath. During the acylation, the temperature of the reaction mixture was kept between 8° C. and 11° C. The reaction was stopped by the successive addition of $CH_3OH$ (300 mL) and 1% NaCl-solution (300 mL). The lower phase was collected and the solvent removed. The oily residue was purified by chromatography using the solvent systems displayed in Table 5.

TABLE 5

| Solvent System | A | B | C | D | E |
|---|---|---|---|---|---|
| hexane | 4 | 3 | 2 | — | — |
| $CHCl_3$ | 1 | 1 | 1 | 7 | 6 |
| ethyl acetate | — | 1 | 2 | 2 | 2 |
| 2-propanol | — | — | — | 1 | 2 |

The product eluted with the systems D and E affording 21 g (0.03 mol, MW 709.14). TLC:$CHCl_3$/ethyl acetate (1:1); $R_f$~0.20. The solvent was removed and the residue was directly taken to methylation.

2.1c N-Methylation of the Acylated Amine

The acylated amine (MW 709.14; 21 g, 0.03 mol) was dissolved in $CHCl_3$ (300 mL) and $CH_3I$ (MW 141.94; 14 g, 0.10 mol). After heating for 60 min at 55° C., the methylation was complete. TLC:$CHCl_3$/2-propanol (1:1); $R_f$~0.10).

2.1d Ion Exchange (Cl- for I-)

The $CHCl_3$-solution of the methylation step was treated with sodium chloride-solution as described above. The iodide was completely exchanged for chloride. The $CHCl_3$-phase was separated. After the addition of ethyl acetate (200 mL), the solvent was removed and the residue (~14 g) was dissolved in $CHCl_3$ (40 mL). The product was precipitated by the addition to the $CHCl_3$ of ethyl acetate (400 mL). The crystals which separated were collected at 4° C. The product was obtained in 50% yield (MW 810.12; 16 g, 0.02 mol). TLC:$CHCl_3$/$CH_3OH$/acetic acid/$H_2O$ (50:40:5:2.5).

Example 3

This example illustrates the synthesis of compounds according to Formula III. The synthesis of compounds having this basic structural motif proceeds according to the generalized set of steps displayed in Scheme 8.

Scheme 8

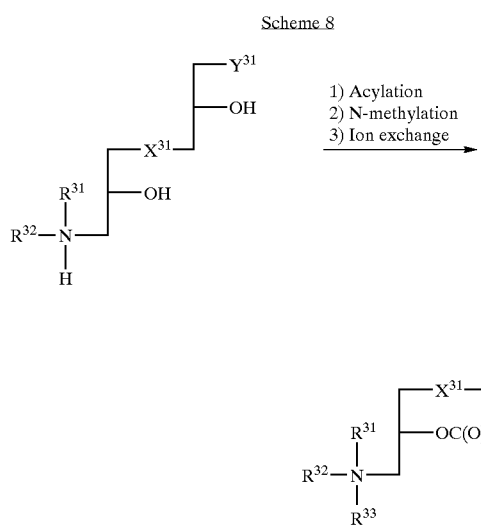

3.1 Synthesis of Compounds Corresponding to Formula III

A family of compounds according to Formula III can be prepared by the procedure outlined in Scheme 9.

Scheme 9

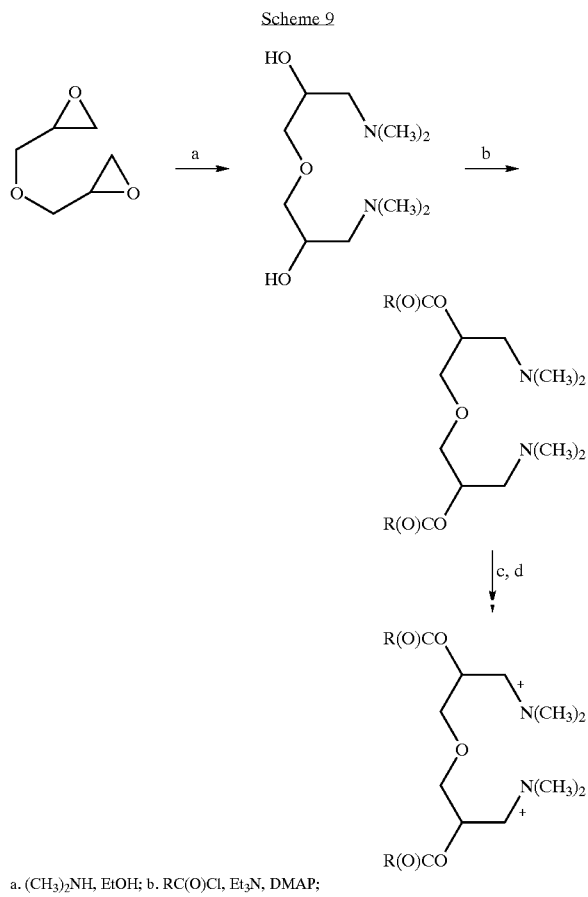

a. $(CH_3)_2NH$, EtOH; b. $RC(O)Cl$, $Et_3N$, DMAP;
c. $CH_3I$, $HCCl_3$; d. ion exchange ($Cl^-$ for $I^-$)

3.1a Synthesis of the Basic Structure

Glycidoglycidol (MW 130.14; 0.2 mol—26 g) was dissolved in 33% dimethylamine (MW 45.08; 1.12 mol) in ethanol (200 mL). The reaction mixture was heated for 1 hr at 60° C. Glycidoglycidol was completely converted to the product (1-dimethylamino-2-hydroxy)-propyl-O,O-3,3-(1-dimethylamino-2-hydroxy)-propyl ether (MW 220.31). The solvent was removed from the reaction mixture by evaporation. The resulting oily residue, ~40 g was purified by chromatography using the solvent systems displayed in Table 6

TABLE 6

| Solvent System | A | B | C |
|---|---|---|---|
| $CHCl_3$ | 100 | 65 | 65 |
| $CH_3OH$ | 15 | 15 | 30 |
| Ammonia (12.5%) | 1 | 1 | 3 |

The product was eluted with the systems B and C, resulting in 30 g of the basic structure (yield 68%). TLC:solvent B; $R_f$=0.2.

3.1b Acylation of the Basic Structure With Myristoyl Chloride

The method described in Example 1.1 was used. The amine from 3.1a (MW 220.31; 11 g, 0.05 mol), triethylamine (MW 101.19; 10.1 g, 0.1 mol) and N,N-dimethylaminopyridine (MW 122.17; 1.6 g, 0.013 mol) were dissolved in $CHCl_3$ (300 mL) with continuous stirring. Stirring was continued and acylation with myristoylchloride (MW 246.82; 24.7 g, 0.1 mol) in $CHCl_3$ (100 mL) was performed by dropwise addition of the acylchloride while taking care that the temperature of the reaction mixture did not exceed 35° C. (cooling with a water bath). After the addition of the acylchloride, the temperature of the reaction mixture was kept at 35° C. for 30 min. The reaction was complete as shown by TLC: $CHCl_3$/2-propanol (1:1); $R_f$=~0.25. When the reaction was complete, $CH_3OH$ (400 mL) and 1% NaCl (400 mL) were added to the reaction mixture. Stirring was continued for 5 min and the lower phase was collected. The solvent was removed and the oily residue was taken directly to methylation.

3.1c N-Methylation of the Acylated Amine

The acylated amine (MW 649.09; 0.05 mol—32.5 g) was dissolved in a mixture of $CHCl_3$ (300 mL) and $CH_3I$ (MW 141.94; 21.3 g, 0.15 mol). After 60 min at 50° C., the methylation was complete. TLC: $CHCl_3$/2-propanol (1:1); starting material, $R_f$~0.25; product, $R_f$~0.05.

3.1d Exchange of Iodide for Chloride

The reaction mixture from the methylation step was treated with NaCl solution as described above for ion exchange. After 5 repeat treatments of the $CHCl_3$ phase with NaCl, the iodide was completely exchanged for chloride. The $CHCl_3$ phase was separated and ethyl acetate (200 mL) were added. After removal of the solvent, the residue (~40 g) was dissolved in $CHCl_3$ (80 mL) and precipitated by the addition of ethyl acetate (800 mL). The crystals were collected at 4° C. The product was obtained in 70% yield (MW 750.07; 26 g, 0.035 mol). TLC:$CHCl_3$/$CH_3OH$/acetic acid/$H_2O$ (50:40:5:2.5); $R_f$=0.05 in.

Scheme 10

3.2 Mixed Chain Analogues
Family I

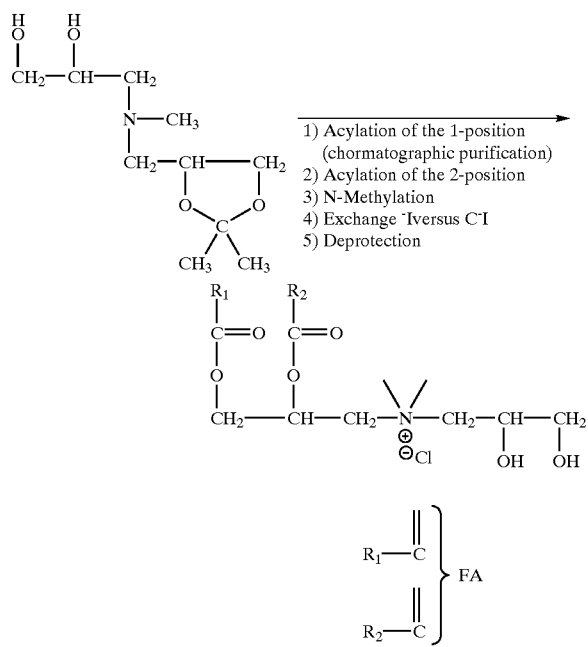

Mixed Chain Analogues

Family I (Mixed Chain)

3.2a Monoacylation of the Basic Structure With Stearoylchloride in Position 1

Mixed Chain Analogoues starting from N-[1-Stearoyl-dihydroxypropyl-(1,2)]-N,N-dimethylamine. Amine (MW 219.28; 0.17 mol—20 g), triethylamine (MW 101.19; 0.11 mol—11 g) and (N,N-dimethyl)-aminopyridine (MW 122.17; 0.02 mol—2.4 g) are dissolved in 200 mL THF. Under continuous stirring stearoylchloride (MW 302.93; 0.1 mol—30.3 g) in 100 mL THF is added dropwise to the reaction mixture at 18 to 20° C. (cooling with a water bath). After 30 min at 20° C., the reaction is completed as demonstrated by TLC in $CHCl_3/CH_3OH$/acetic acid/$H_2O$ 600:60:20:5 (by volume: Educt, $R_f$ 0.55; Monostearoly-compound, $R_f$ 0.15; Distearoyl-compound, $R_f$ 0.40. For work-up, diisopropylether, 300 mL and water, 300 mL are added and the mixture is thoroughly shaken in a separating funnel. The upper layer contains the product. It is freed from solvent and the residue, ~50 g, is dissolved in 400 mL acetone and stored at 10° C. for crystallization. The crystals contain mainly the diproduct, N-[1,2-distearoyl-dihydroxypropyl-(1,2)]-N-methyl-N-(1,2-isopropylidene-dihydroxypropyl-(1,2)-amine. The filtrate contains the monoproduct. It is removed from solvent. The product, 35 g of a waxy material, is purified by chromatography: 220 g Silicagel (Merck) in $CHCl_3$/Ethylacetate 400:600 (per volume) is used for the crhomatographic separation.

| Solvent Systems (for elution) | | | |
|---|---|---|---|
| $CHCL_3$ | Ethylacetate | 2-Propanol | $CH_3OH$ |
| A 400 | 600 | — | — |
| B 400 | 500 | 100 | — |
| C 400 | 400 | — | 200 |

The product is eluted with solvent B. The pure product, N-1-Stearoyl-dihydroxypropyl-(1,2)-N-methyl-N-[1,2-isopropylidene-dihydroxypropyl-(1,2)]-amine (MW 453.75) is obtained in 55% yield (0.055 mol—25 g) based on stearoylchloride 3.2b Second Acylation Step (Introduction of oleic acid, lauric acid or erucic acid into the 2-position of the amine)

The product of the acylation of the 1-position (MW 453.75; 0.055 mol—25 g) is divided in 3 parts of 0.081 mol, corresponding with 8.2 g and dissolved in 100 mL THF. To each of the solutions is added triethylamine (MW 101.19; 0.022 mol—2.2 g) and (N,N-dimethyl)-amino-pyridine (MW 122.17; 0.003 mol—370 mg). The dropwise addition of the different acylchlorides under continuous stirring 35° C. is performed in 100 mL THF with oleoylchloride (MW 300.91; 0.02 mol—6 g), erucoylchloride (MW 357.02; 0.02 mol—7.1 g) or lauroylchloride (MW 218.77; 0.02 mol—4.4 g). After 30 min, the reactions are completed as shown by TLC in $CHCl_3$/ethylacetate 1:1 (by volume): Educt, $R_f$ 0.05; products, $R_f$ ~0.65.

The three different acylations are worked-up separately by adding $CH_3OH$, 100 mL, diisopropylether, 200 mL, water, 200 mL and cyclohexane, 200 mL. The upper phase contains the product. It is freed from solvent and directly taken to methylation.

3.2c N-Methylation of the Acylated Amine

The acylated amines 1-stearoyl-2-oleoyl (MW 806.30; 0.02 mol—15 g); 1-stearoyl-2-erucoyl (MW 750.19; 0.02 mol—16 g); 1-stearoyl-2-lauroyl (MW 668.05; 0.02 mol—14 g), are dissolved in $CHCl_3$ in three different flasks, $CH_3I$ (MW 141.94; 0.15 mol —21 g) is added and heated after sealing to 50° C. The reaction is complete after 2 hrs as shown by TLC in $CHCl_3$/1:1 (per volume): Educt, $R_f$ 0.65; product, $R_f$ 0.05.

3.2d Exchange Iodide Versus Chloride

The chloroform phases containing the permethylated products are treated separately with NaCl as described for the single acid compounds.

3.2e Deprotection

Deprotection is also performed as described above and also the final purification by column chromatography:

| (stearoyl/oleoyl) | (stearoyl/erucoyl) | (stearoyl/laurcoyl) |
|---|---|---|
| MW 760.62 | MW 816.73 | MW 678.47 |
| yield: 0.015 mol - 11.3 g | yield: 0.016 mol - 13 g | yield: 0.012 mol - 8 g |
| (75%) | (80%) | (60%) |

Example 4

This example provides both a method for preparing a cationic lipid vesicle which is loaded with a nucleic acid and a test of the effectiveness of this lipid vesicle at delivering the nucleic acid in vivo.

4.1 Experimental Protocol

Two mice studies have been performed for the evaluation of cationic lipids of the present invention, in comparison with DOTIM. In brief, the lipid combinations were tested as carriers for gene transfer by intravenous delivery in ICR female mice (25 g), and expression was determined using the plasmid p4119 containing the CAT reporter gene under the control of the HCMV promoter. The lipids were dissolved in a mixture of chloroform and methanol (1.1). Lipid films of cationic and neutral lipid at a 1:1 molar ratio were formed with a rotary evaporator. The films were hydrated with 5% dextrose in water (D5W) at room temperature and extruded through a series of membranes having pore sizes of 400 nm, 200 nm, and 50 nm.

4.1a Preparation of DNA-liposomes

Figure 10:
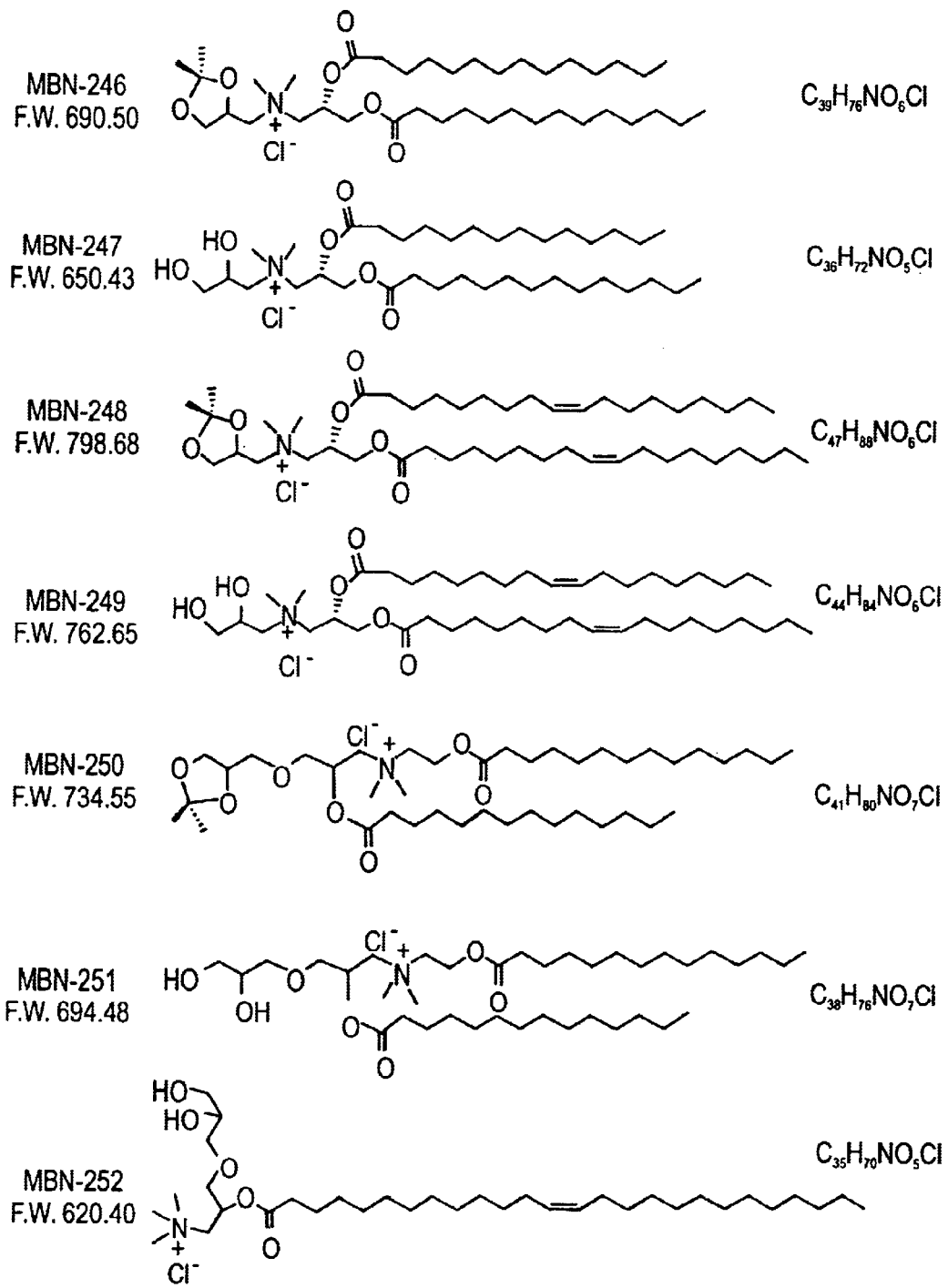
FIG. 10 provides details on lipid structures.

DNA-liposome complexes were prepared at a 1:10 DNA::cationic lipid ratio (mg DNA per µmole cationic lipid) by adding the DNA, in a solution at 0.625 mg/mL concentration in D5W to the solution of liposomes, in an equal volume, with constant stirring, using a Hamilton Dilutor 540B (Hamilton, Reno, Nev.). The lipids used were MBN 246, 247, 248, 249, 250, 251 and 252 (FIG. 10). MBN 249 was used in a 1:10 ratio with cholesterol. MBN 250 was used in a 1:10 ratio with DLPE. The DNA solution was 0.3125 mg/mL DNA in D5W. The resulting complexes were sized using a Submicron Particle Sizer 370 (Nicomp, Santa Barbara, Calif.). Zeta potential was determined by a Zeta Plus, Zeta Potential Analyzer (Brookhaven Instruments Corp.).

A total of 5 mice were tested per group. A dose of 62.5 mg p4119 plasmid DNA 200 µL was injected by tail vein per mouse. The lung, heart, liver, and spleen were harvested 24 h after injection. Each organ was homogenized in 1.0 mL of 5 mM EDTA/0.25M Tris-HCl pH 7.8 containing 5 µg/mL Aprotinin (Boehringer Mannheim, Indianapolis, Ind.), 5 µg/mL Leupeptin (Boehringer Mannheim, Indianapolis, Ind.), and 5 mM PMSF (Boehringer Mannheim, Indianapolis, Ind.), The resulting extracts were centrifuged and aliquots of the supernatant were removed for protein analysis, utilizing a bicinchoninic acid based reagent kit (Pierce, Rockford, Ill.). For CAT ELISA assay, each well of Corning EIA/RIA 96 well plates (VWR, West Chester, Pa.) was coated overnight at 4–8 C with 0.6 µg of Rabbit anti-CAT antibody (5 Prime-3 Prime, Boulder, Colo.) diluted in 50 µl of 50 mM sodium bicarbonate buffer pH 9.5. The coated plate was incubated at room temperature for one hour with 200 µl PBS pH 7.4 containing 5% (w/v) Carnation non-fat dry milk and 0.2% (v/v) Tween-20 (Blotto) to block all non-specific binding sites. After washing four times in wash buffer containing 0.2% Tween-20 in PBS, the plate was incubated for an hour at 37 C with 50 µl sample. For each sample, a 1:2 serial dilution was performed in Blotto to ensure the reading to fall in the readable range of the standard curve. After washing four times in wash buffer, the plate was incubated for 45 minutes at 37 C in 50 µl Digoxigenin labeled sheep anti-CAT antibody (Boehringer Mannheim, Indianapolis, Ind.) diluted 1:100 in Blotto. The plate was washed again four times in wash buffer. Finally, it was incubated for 45 minutes at 37° C. in 50 µl peroxidase conjugated Fab fragment of sheep anti-DIG antibody (Boehringer Mannheim), diluted 1:400 in Blotto. After washing four times in wash buffer, color reaction was developed in 150 µl 5 mg/mL ABTS in 0.1 M citrate buffer pH 4.2 containing 0.03% hydrogen peroxide. Color changes were red on a SPECTRAmax 250 using Softmax Pro V.1.2 software (Molecular Devices, Sunnyvale, Calif.) at A405–A490. Result reading from each sample was calculated by the interpolation with a standard curve created by a 1:2 serial dilution of standard CAT enzyme of known concentration (Boehringer Mannheim).

4.2 Results

Figure 9:
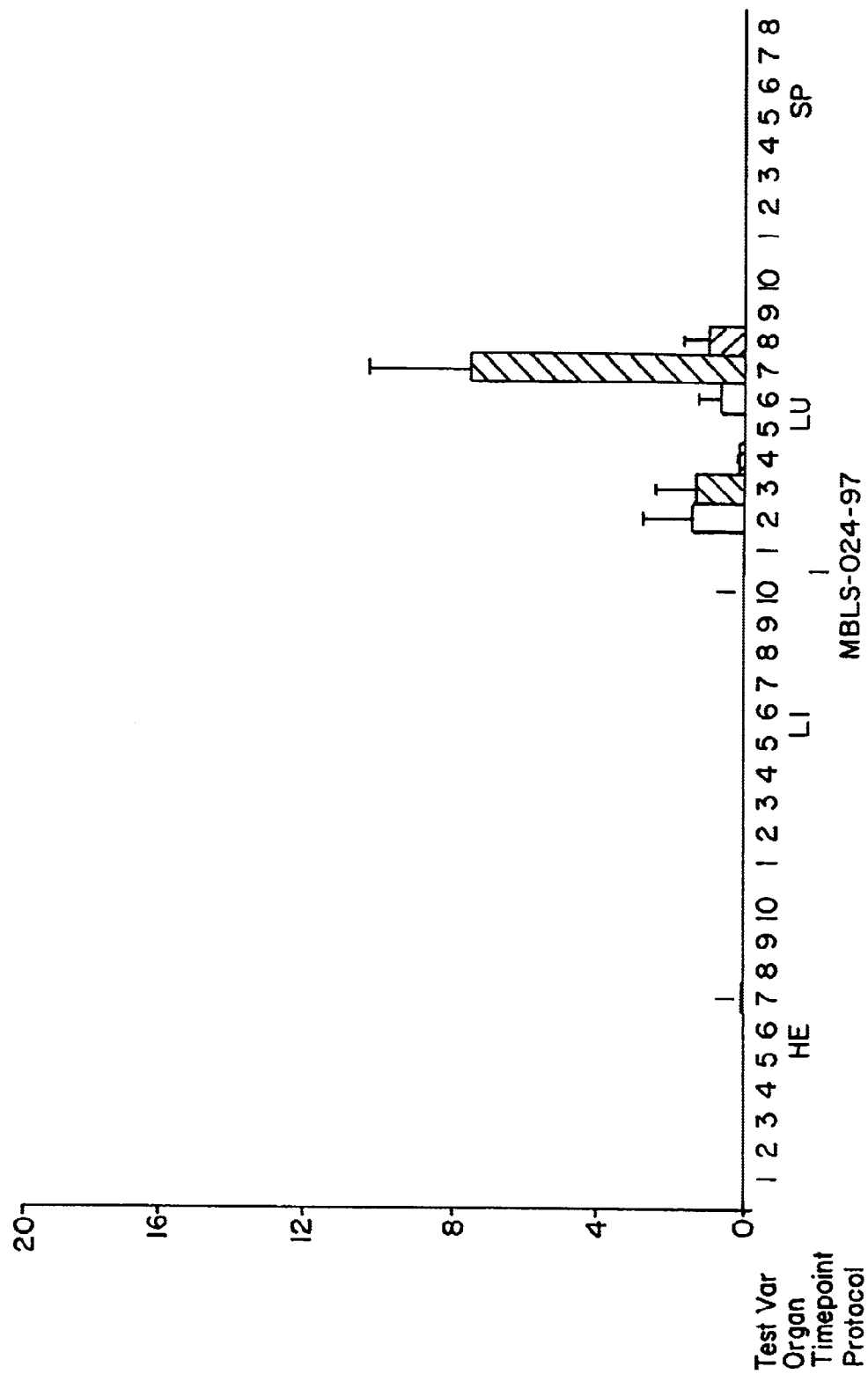
FIG. 9 provides details on the effectiveness of lipid vesicles at delivering nucleic acid in vivo.

The results of the experiments are shown in FIG. 9. Sample 1 is D5W, sample 2 is DOTIM:Cholesterol (1:6 DNA:cationic lipid ratio), sample 3 is DOTIM:DLPE (1:10 DNA cationic lipid ratio), sample 4 is MBN246:Cholesterol (1:10), sample 5 is MBN247:Cholesterol (1:10), sample 6 is MBN248:Cholesterol (1:10), sample 7 is MBN249:Cholesterol (1:10), sample 8 is MBN250:DLPE (1:10), sample 9 is MBN251:Cholesterol (1:10) and sample 10 is MBN252:Cholesterol (1:10) (see FIG. 10 for lipid structures). It can be seen that the DNA-lipid complexes of the invention provided high levels of CAT protein in lung tissue.

Example 5

This example comprises the CAT expression in mice lungs of different formulations.

A second protocol was performed as in Example 4, to compare MBN 249 with the ether derivative MBN 305 (Scheme 5). MBN275, which is the ether derivative of DOTIM ether was used as the positive control. Five animals per group were used for screening. The expression was normalized relative to total soluble protein.

Figure 7:
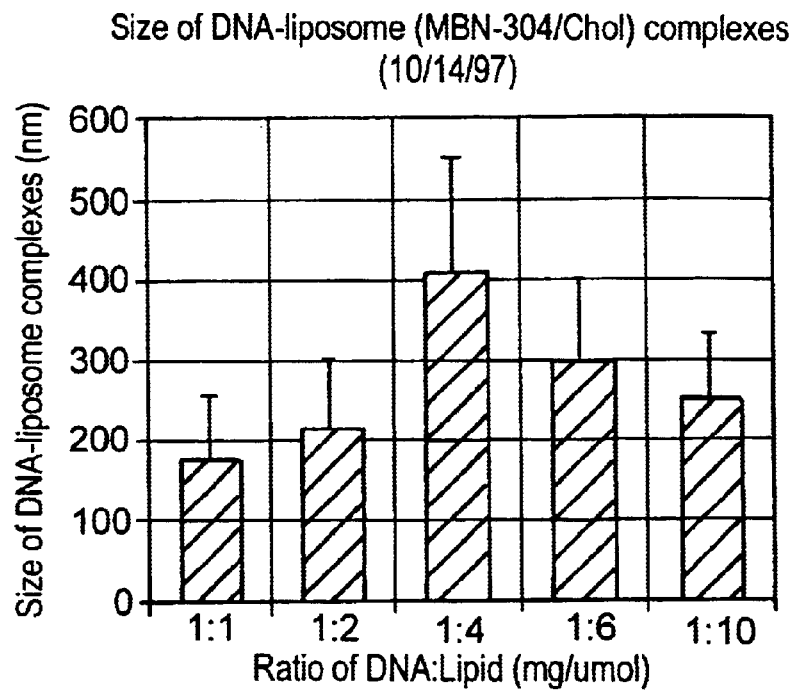
FIG. 7 provides size of DNA-liposome complexes.
Figure 7:
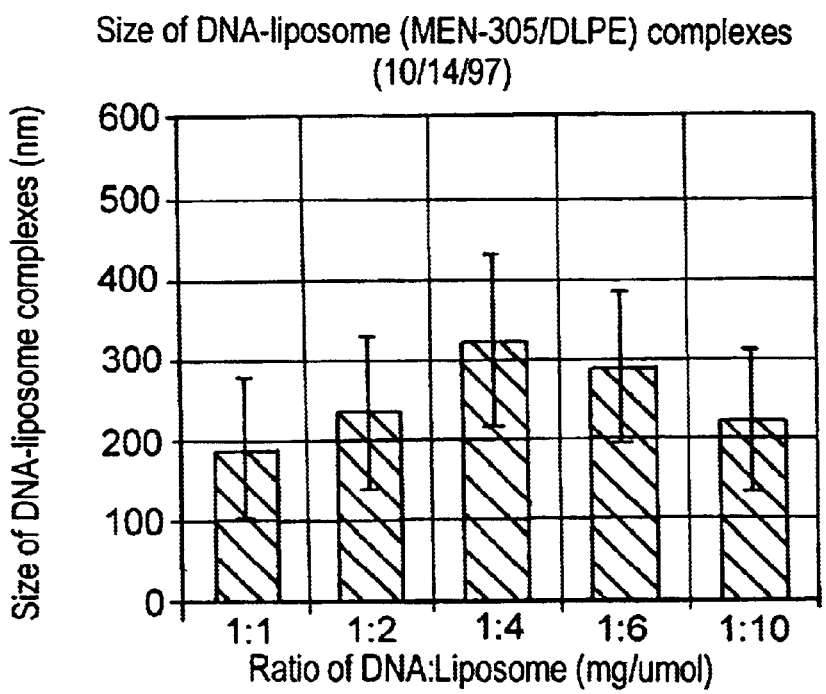
Figure 8:
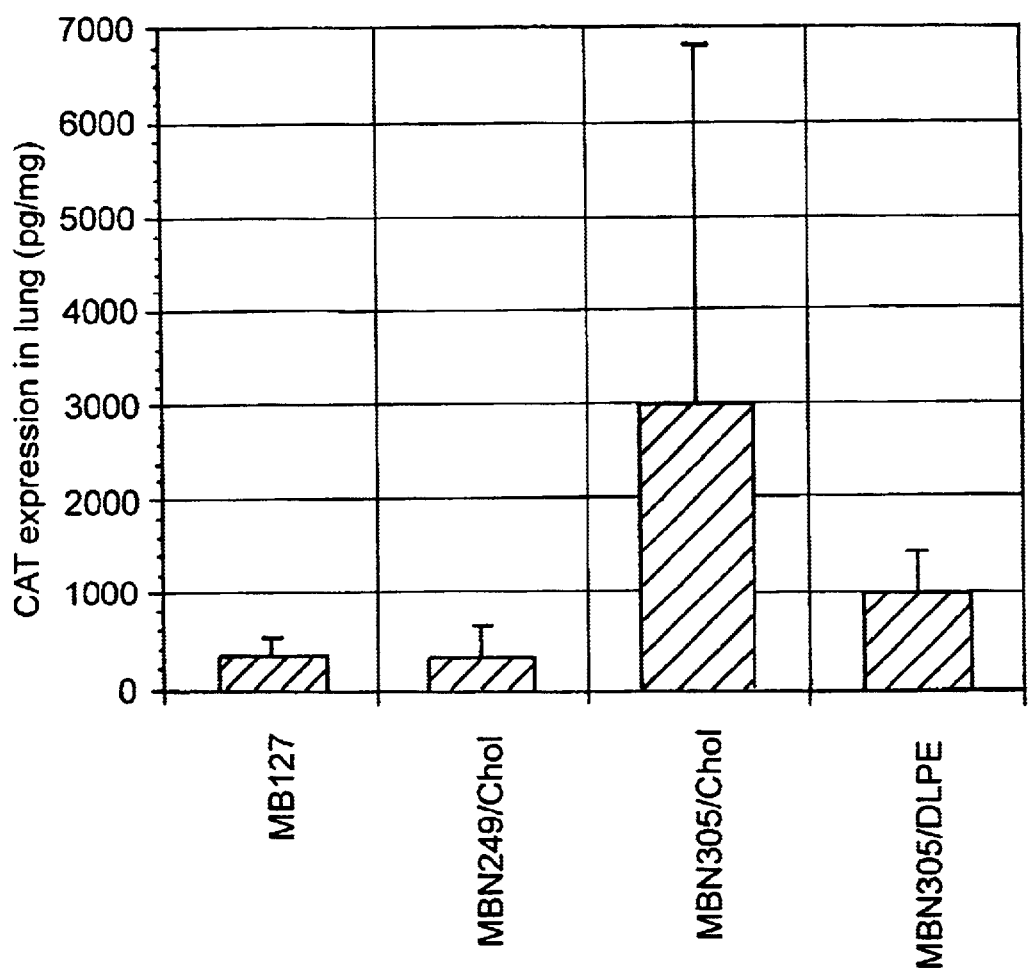
FIG. 8 provides CAT expression in lung following I.V. administration.

It was shown that the new lipid MBN305 forms liposomes easily. After extrusion, the diameter of the MBN305/Chol liposome was 109±37 nm, and that of the MBN305/DLPE liposome was 79±nm. The size of the DNA-liposome complexes varies with the DNA/cationic lipid ratio as shown in FIG. 7. In addition, it was shown that CAT expression in mice lungs of formulation DNA:MBN 305/Chol (1:6) is nine-fold higher than that of formulation MBN275:Chol (1:6) (FIG. 8). Formulation DNA:MBN305/DLPE (1:6) showed a three-fold higher transfection level than MBN275:Chol (1:6) DNA:MBN249/Chol (1:6) showed about the same expression level as MBN275:Chol (1:6) in this protocol. These results indicates that linker group not only affects the stability of the lipids, but also influence the transfection efficacy. Cholesteral is the preferred helper lipid with MBN305. The ether linkage increased transfection activity for this lipid family.

Although the invention has been described with reference to preferred embodiments and examples thereof, the scope of the present invention is not limited only to those described embodiments. As will be apparent to persons skilled in the art, modifications and adaptations to the above-described invention can be made without departing from the spirit and scope of the invention, which is defined and circumscribed by the appended claims.

What is claimed is:

1. A compound having the formula:

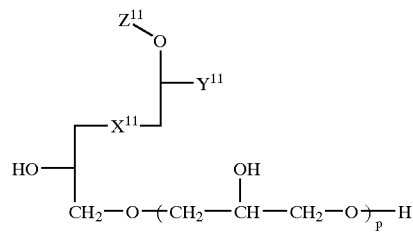

wherein:

X$^{11}$ represents $$-\underset{\underset{R^{12}}{|}}{\overset{\overset{R^{11}}{|}}{N^+}}-$$

R$^{11}$ and R$^{12}$ are each independently a C$_1$–C$_6$ alkyl group;
Z$^{11}$ is selected from the group consisting of a saturated C$_1$–C$_{26}$ alkyl group, an unsaturated C$_3$–C$_{26}$ alkyl group, a saturated C$_2$–C$_{26}$ acyl group, or an unsaturated C$_4$–C$_{26}$ acyl group;
p is 0 to 6;
Y$^{11}$ is —CH$_2$—O—R; and
R is selected from the group consisting of a saturated C$_1$–C$_{26}$ alkyl group, an unsaturated C$_3$–C$_{26}$ alkyl group, a saturated C$_2$–C$_{26}$ acyl group, or an unsaturated C$_4$–C$_{26}$ acyl group; providing at least one of either Z$^{11}$ or R contains a group having at least 14 carbon atoms.

2. A compound in accordance with claim 1, wherein p=0.

3. A compound in accordance with claim 2, wherein X$^{11}$ is —N$^+$(CH$_3$)$_2$—.

4. A compound in accordance with claim 2, wherein X$^{11}$ is —N$^+$(CH$_3$)$_2$—,
Z$^{11}$ is selected from the group consisting of a saturated or unsaturated C$_8$–C$_{22}$ alkyl group, or a saturated or unsaturated C$_4$–C$_{22}$ acyl group;
Y$^{11}$ is —CH$_2$—O—R; and
R is selected from the group consisting of a saturated or unsaturated C$_8$–C$_{22}$ alkyl group, or a saturated or unsaturated C$_4$–C$_{22}$ acyl group.

5. A compound in accordance with claim 4, wherein R is a saturated or unsaturated C$_{18}$ alkyl or acyl group.

6. A compound in accordance with claim 5, wherein R is —CH$_2$(CH$_2$)$_7$CH═CH(CH$_2$)$_7$CH$_3$.

7. A compound in accordance with claim 1, wherein R and Z$^{11}$ are —CH$_2$(CH$_2$)$_7$CH═CH(CH$_2$)$_7$CH$_3$.

8. A compound in accordance with claim 1, wherein Z$^{11}$ is selected from the group consisting of a saturated C$_8$–C$_{26}$ alkyl group, an unsaturated C$_8$–C$_{26}$ alkyl group, a saturated C$_2$–C$_{26}$ acyl group, or an unsaturated C$_4$–C$_{26}$ acyl group.

9. A compound in accordance with claim 1, wherein Y$^{11}$ is selected from the group consisting of a saturated C$_8$–C$_{26}$ alkyl group, an unsaturated C$_8$–C$_{26}$ alkyl group, a saturated C$_2$–C$_{26}$ acyl group, or an unsaturated C$_4$–C$_{26}$ acyl group.

10. A compound in accordance with claim 2 wherein Z$^{11}$ is selected from the group consisting of a saturated C$_8$–C$_{26}$ alkyl group, an unsaturated C$_8$–C$_{26}$ alkyl group, a saturated C$_2$–C$_{26}$ acyl group, or an unsaturated C$_4$–C$_{26}$ acyl group.

11. A compound in accordance with claim 2 wherein Y$^{11}$ is selected from the group consisting of a saturated C$_8$–C$_{26}$ alkyl group, an unsaturated C$_8$–C$_{26}$ alkyl group, a saturated C$_2$–C$_{26}$ acyl group, or an unsaturated C$_4$–C$_{26}$ acyl group.

12. A compound having the formula:

[Chemical structure: HO-CH$_2$-CH(OH)-CH$_2$-N(CH$_3$)-CH$_2$-CH(OR)-CH$_2$-OR]

wherein each R is independently selected from the group consisting of a saturated C$_8$–C$_{26}$ alkyl group, an unsaturated C$_8$–C$_{26}$ alkyl group, a saturated C$_2$–C$_{26}$ acyl group, or an unsaturated C$_4$–C$_{26}$ acyl group.

13. The compound of claim 12 wherein each R is a saturated C$_8$–C$_{22}$ alkyl group derived from a fatty acid selected from the group consisting of: lauryl (C12:0), myristyl (C14:0), palmityl (C16:0), stearyl (C18:0), arachidyl (C20:0), and behenyl (C22:0).

14. The compound of claim 12 wherein each R is an unsaturated C$_8$–C$_{20}$ alkyl group derived from a hydrocarbon selected from the group consisting of: oleyl (C18:1,cis-9), linoleyl (C18:2,cis-9,12), elaidyl (C18:1,trans-9), linolelaidyl (C18:2,trans-9,12), and eicosenyl (C20:1,cis-11).

15. The compound of claim 14 wherein each R is —CH$_2$(CH$_2$)$_7$CH═CH(CH$_2$)$_7$CH$_3$.

16. The compound of claim 12 wherein each R is a saturated C$_2$–C$_{26}$ acyl group or an unsaturated C$_4$–C$_{26}$ acyl group.

17. The compound of claim 16 wherein each R is a C$_2$–C$_{22}$ acyl group selected from the group consisting of acetyl, lauroyl, palmitoyl, stearoyl, myristoyl, oleoyl, and erucoyl.

18. The compound of claim 12 selected from the group consisting of a compound of the following formula (MBN249)

[Chemical structure of MBN249]

and a compound of the following formula (MBN305)

[Chemical structure of MBN305]

* * * * *